US010861152B2

(12) United States Patent
Madabhushi et al.

(10) Patent No.: US 10,861,152 B2
(45) Date of Patent: Dec. 8, 2020

(54) VASCULAR NETWORK ORGANIZATION VIA HOUGH TRANSFORM (VANGOGH): A RADIOMIC BIOMARKER FOR DIAGNOSIS AND TREATMENT RESPONSE

(71) Applicant: Case Western Reserve University, Cleveland, OH (US)

(72) Inventors: Anant Madabhushi, Shaker Heights, OH (US); Nathaniel Braman, Cleveland, OH (US); Prateek Prasanna, Cleveland, OH (US)

(73) Assignee: Case Western Reserve University, Cleveland, OH (US)

( * ) Notice: Subject to any disclaimer, the term of this patent is extended or adjusted under 35 U.S.C. 154(b) by 82 days.

(21) Appl. No.: 16/354,504

(22) Filed: Mar. 15, 2019

(65) Prior Publication Data
US 2019/0287243 A1    Sep. 19, 2019

Related U.S. Application Data

(60) Provisional application No. 62/643,917, filed on Mar. 16, 2018.

(51) Int. Cl.
*G06K 9/00* (2006.01)
*G06T 7/00* (2017.01)
(Continued)

(52) U.S. Cl.
CPC .......... *G06T 7/0012* (2013.01); *A61B 5/7253* (2013.01); *A61B 5/7267* (2013.01); *G06K 9/4633* (2013.01); *G06K 9/628* (2013.01); *G06K 9/6228* (2013.01); *G06K 9/6277* (2013.01); *G06K 9/6286* (2013.01); *G06T 7/11* (2017.01);
(Continued)

(58) Field of Classification Search
CPC ............................................. G06T 2207/10096
See application file for complete search history.

(56) References Cited

U.S. PATENT DOCUMENTS 8,090,164 B2 *   1/2012   Bullitt .................. G06T 7/0014
                                                            382/128
2008/0292169 A1 *  11/2008   Wang ...................... G06T 7/174
                                                            382/131
(Continued)

*Primary Examiner* — Oneal R Mistry
(74) *Attorney, Agent, or Firm* — Eschweiler & Potashnik, LLC

(57) ABSTRACT

Embodiments access a radiological image of tissue having a tumoral volume and a peritumoral volume; define a vasculature associated with the tumoral volume; generate a Cartesian two-dimensional (2D) vessel network representation; compute a first set of localized Hough transforms based on the Cartesian 2D vessel network representation; generate a first aggregated set of peak orientations based on the first set of Hough transforms; generate a spherical 2D vessel network representation; compute a second set of localized Hough transforms based on the spherical 2D vessel network representation; generate a second aggregated set of peak orientations based on the second set of Hough transforms; generate a vascular network organization descriptor based on the aggregated peak orientations; compute a probability that the tissue is a member of a positive class based on the vascular network organization descriptor; classify the ROI based on the probability; and display the classification.

22 Claims, 15 Drawing Sheets

(51) Int. Cl.
*G06T 7/62* (2017.01)
*G06K 9/46* (2006.01)
*G06K 9/62* (2006.01)
*G06T 7/70* (2017.01)
*G06T 15/08* (2011.01)
*A61B 5/00* (2006.01)
*G06T 7/11* (2017.01)
*G06T 7/187* (2017.01)

(52) U.S. Cl.
CPC .......... *G06T 7/62* (2017.01); *G06T 7/70* (2017.01); *G06T 15/08* (2013.01); *G06K 2209/05* (2013.01); *G06T 7/187* (2017.01); *G06T 2207/10081* (2013.01); *G06T 2207/10088* (2013.01); *G06T 2207/20044* (2013.01); *G06T 2207/20061* (2013.01); *G06T 2207/20076* (2013.01); *G06T 2207/20081* (2013.01); *G06T 2207/20084* (2013.01); *G06T 2207/20116* (2013.01); *G06T 2207/20152* (2013.01); *G06T 2207/30064* (2013.01); *G06T 2207/30068* (2013.01); *G06T 2207/30096* (2013.01); *G06T 2207/30101* (2013.01)

(56) References Cited

U.S. PATENT DOCUMENTS

| 2012/0201445 A1* | 8/2012 | El-Baz | G06K 9/621 382/133 |
| 2018/0322635 A1* | 11/2018 | Guo | G06K 9/3233 |
| 2020/0085382 A1* | 3/2020 | Taerum | G06N 3/084 |
| 2020/0219237 A1* | 7/2020 | Ramsay | G16H 30/40 |

* cited by examiner

Spherical Vessel Maps:
Vessel position relative to tumor center and surface

VASCULAR NETWORK ORGANIZATION VIA HOUGH TRANSFORM (VANGOGH): A RADIOMIC BIOMARKER FOR DIAGNOSIS AND TREATMENT RESPONSE

CROSS REFERENCE TO RELATED APPLICATIONS

This application claims the benefit of U.S. Provisional Application 62/643,917 filed Mar. 16, 2018, which is incorporated by reference herein in its entirety.

FEDERAL FUNDING NOTICE

This invention was made with government support under the grant(s) F31CA221383-01A1, 1U24CA199374-01, R01CA202752-01A1, R01CA208236-01A1, R21CA179327-01, R21CA195152-01, RO1 DK098503-02, 1C06-RR12463-01, PC120857, LC130463, and T32EB007509 awarded by the National Institutes of Health Also grant W81XWH-16-1-0329 awarded by the Department of Defense. The government has certain rights in the invention.

BACKGROUND

Tumor-induced angiogenesis is one of the most important mechanisms of a tumor's adaptation to changes in nutrient requirement. The angiogenic activity of certain tumors may be predictive of a patient's ultimate response to therapeutic intervention. Differences in vessel arrangement and corresponding convolutedness may exist between tumors that appear phenotypically similar, but respond differently to treatment. Existing textural radiomics and deep learning-based approaches have been shown to distinguish disease aggressiveness and assess therapeutic response, however, these descriptors do not specifically interpret differences in vessel characteristics. Moreover, existing approaches attempt to model disease characteristics just within tumor confines, or immediately outside the tumor boundary, but do not consider explicit parenchymal vessel morphology. Thus, an improved approach to discriminating between tumors that will respond to treatment or will not respond to treatment based on differences in vessel arrangement and corresponding convolutedness would be advantageous.

BRIEF DESCRIPTION OF THE DRAWINGS

The accompanying drawings, which are incorporated in and constitute a part of the specification, illustrate various example operations, apparatus, methods, and other example embodiments of various aspects of the invention. It will be appreciated that the illustrated element boundaries (e.g., boxes, groups of boxes, or other shapes) in the figures represent one example of the boundaries. One of ordinary skill in the art will appreciate that, in some examples, one element may be designed as multiple elements or that multiple elements may be designed as one element. In some examples, an element shown as an internal component of another element may be implemented as an external component and vice versa. Furthermore, elements may not be drawn to scale.

DETAILED DESCRIPTION

Figure 1:
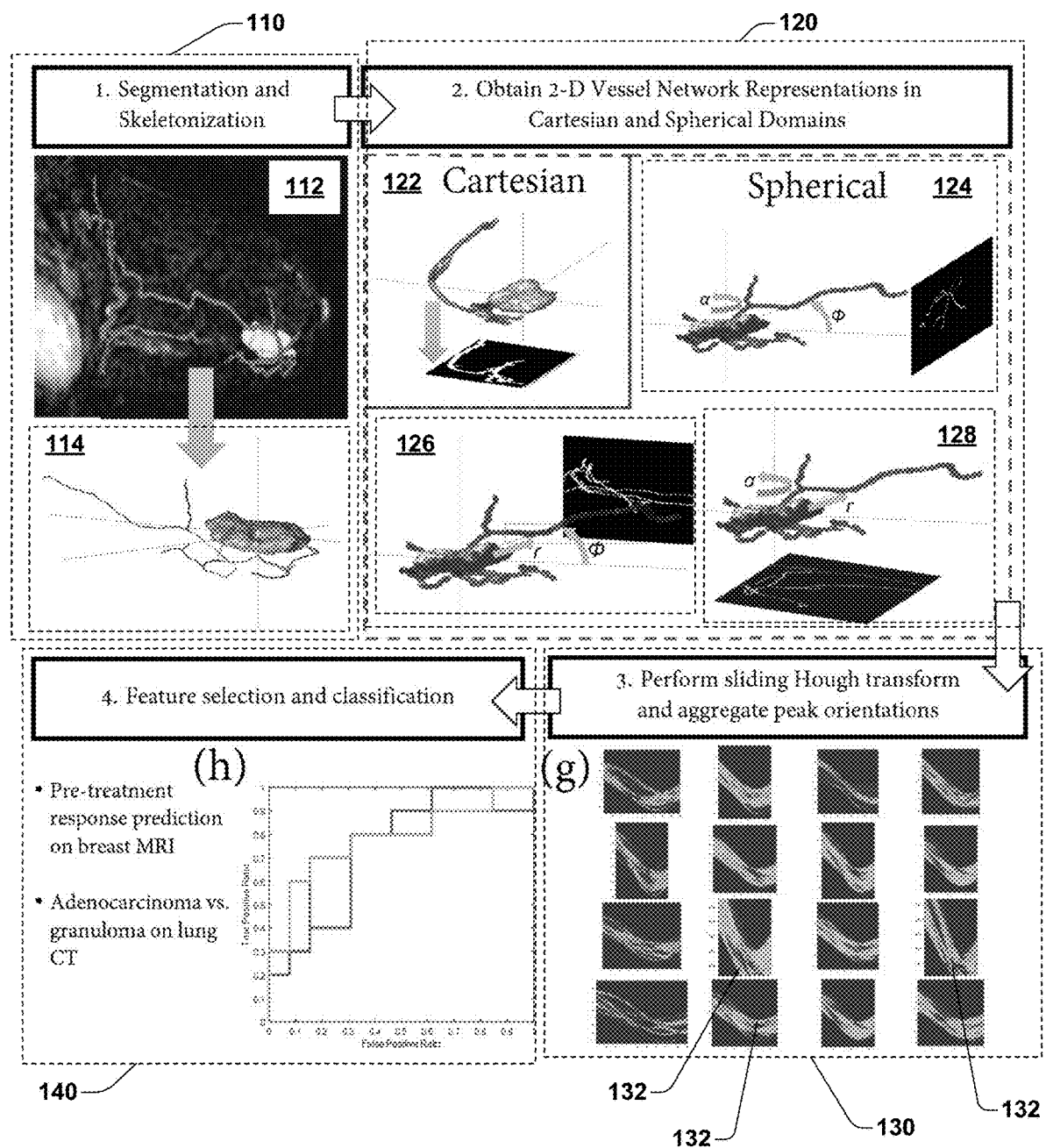
FIG. 1 is a workflow diagram for modelling the architectural disorder of a vascular architecture associated with a tumor or lesion.

Angiogenesis is the process by which a tumor hijacks the body's machinery for creating new vasculature in order to redirect blood flow to itself. Angiogenesis plays an important role in determining tumor response to chemotherapy or radiation therapy. Stimulatory signals, such as vascular endothelial growth factor (VEGF) expression, result in neovascularization, leading to sprouting and irregular blood vessels (i.e., erratic angiogenesis). The associated tortuosity and leakiness affects the course of disease progression, and may affect response to therapeutic interventions. A more convoluted tumor vasculature may constrict the delivery of therapeutic drugs to the lesion, thereby resulting in potentially worse prognosis or treatment response. Existing approaches to disease diagnosis or prediction of tumor treatment response are limited to the tumor or to associated parenchyma, and do not directly target biological aspects of the tumor microenvironment, including vasculature.

Embodiments model the architectural disorder of a tumor's (or lesion's) vascular network by computing local measures of vessel curvature in the Hough parameter space. Embodiments compute an image-based descriptor of vascular network organization via Hough transform (VaNgOGH) which characterizes chaotic vasculature associated with tumor-induced angiogenesis, thus also capturing functional attributes of the tumor. Embodiments define abnormal vessel arrangements across multiple planes and projections, and relative to the tumor core and tumor boundary. Embodiments compute and analyze projections of vascular segmentation along different planes in Cartesian and in spherical coordinates. Embodiments compute localized Hough transforms to identify dominant peaks in the accumulator space. Embodiments compute features that characterize the vessel network in the Cartesian domain, which captures disorder in the plane of image acquisition. Embodiments compute features that characterize the vessel network in the spherical domain, which captures deflections of neighboring vasculature towards the tumor centroid due to angiogenesis. Embodiments, in the spherical domain, compute the VaNgOGH descriptor beyond the tumor, and summarize across regions to capture the magnitude of the tumor's angiogenic influence. In one embodiment, the VaNgOGH descriptor is computed within annular bands of increasing radius within the peritumoral region. The VaNgOGH descriptor includes first order statistics of maximum Hough peak orientations computed in a sliding fashion across vessel projections that summarize vasculature orientation in the XY plane, distance from the tumor vs. azimuthal rotation, distance from the tumor vs. elevation angle, and azimuthal rotation vs. elevation angle. Embodiments classify a region of interest (ROI) into a positive or negative class based on the VaNgOGH descriptor. In one embodiment, the ROI is an ROI demonstrating breast cancer (BCa) and embodiments classify the ROI as likely to experience pathological complete response (pCR) or unlikely to experience pCR (non-pCR) to chemotherapy on dynamic contrast enhanced magnetic resonance imaging (DCE-MRI) imagery. In another embodiment, the ROI is an ROI of a region of tissue demonstrating lung nodules, and embodiments classify a lung nodule as a benign granuloma or as a malignant adenocarcinoma on non-contrast computed tomography (CT) imagery.

One example embodiment is now described in more detail. In this example, embodiments define an image scene I as I=(C, f), where I is a spatial grid C of voxels c∈ C in a three-dimensional (3D) space $\mathbb{R}^3$. Each voxel, c∈ C, is associated with an intensity value f (c). $I_T$ and $I_P$ correspond to the intra-tumoral and surrounding peritumoral parenchyma sub-volumes within every I, respectively, such that $[I_T, I_P] \subset I$. Embodiments divide the sub-volume $I_P$ into uniformly sized annular sub-volumes $I_N^j$, where j is the number of uniformly-sized annular bands, such that j∈ {1, ..., k}, and k is a user-defined proximity parameter dependent on the distance g from the tumor margin. In this example, uniformly sized means an equal distance between the boundary of each successive ring. For each I, there exists a corresponding tumor segmentation T and vessel segmentation V.

FIG. 1 is a workflow diagram for modelling the architectural disorder of a vascular architecture associated with a tumor or lesion. Embodiments segment and skeletonize a tumor and vasculature, illustrated at 110. A segmentation algorithm is applied to I, yielding a volume T containing the tumor, and a volume V containing the surrounding tumor-associated vasculature, illustrated at 112. T is subtracted from V to ensure that there are no residual tumor voxels within the segmented vasculature. In this example, a fast marching approach is employed to compute the centerlines of vessels within V, forming S: a series of points in 3-dimensional Cartesian space comprising the medial axis skeleton of V, illustrated at 114.

Figure 4:
FIG. 4 illustrates a tumor and vasculature segmented from DCE-MRI subtraction images.

FIG. 4 illustrates an example tumor and vasculature segmented from MRI subtraction images. A tumor is indicated at 410. An associated vasculature is indicated at 420.

Embodiments obtain two-dimensional (2D) vessel network representations in the Cartesian domain and in the spherical domain, as illustrated at 120. In the Cartesian domain, S is projected along the plane of image acquisition, z, to obtain a 2-dimensional representation of the vasculature, $V_{xy}$, which depicts the vascular network in the XY plane, as illustrated at 122.

Figure 5:
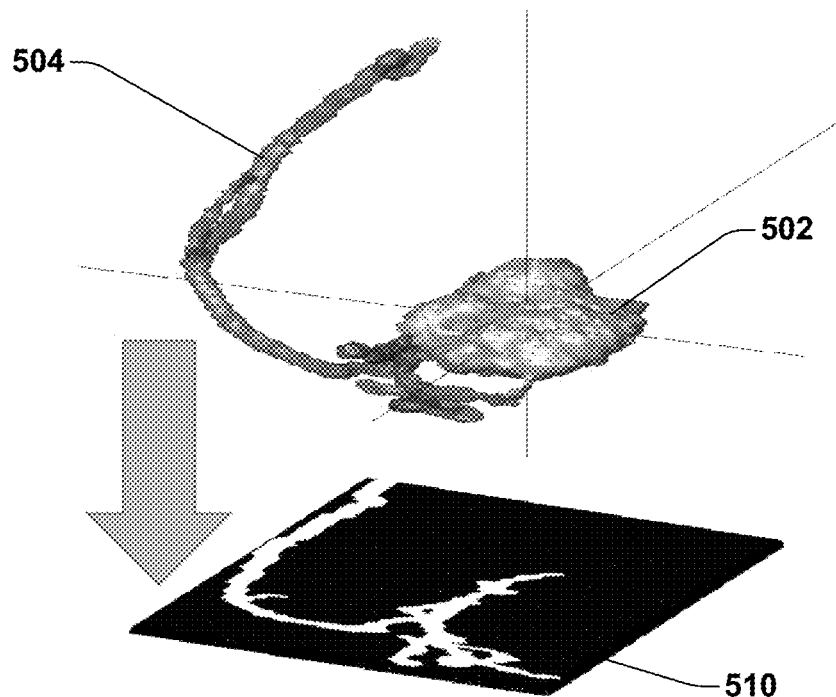
FIG. 5 illustrates a Cartesian vessel map.

FIG. 5 illustrates an example Cartesian vessel map. FIG. 5 includes a tumor region 502 and vasculature 504. FIG. 5 further illustrates a 2D representation 510 of the vasculature 504, in the XY plane.

In the spherical domain, the vascular network is converted to spherical coordinates and projected along each spherical axis to yield three 2-D representations of 3-D vessel orientation with respect to the tumor centroid. Each point within S is converted to its spherical coordinates relative to the tumor centroid, D. Let xD, yD, and zD represent the distance from D of a point $S_i$ within S along the corresponding Cartesian axes. Each Si then corresponds to an azimuth α and an elevation φ, indicating rotation around the z-axis and angle from the XY-plane, respectively, such that $$\alpha = \arctan\left(\frac{yD}{xD}\right) \text{ and } \phi = \arctan\left(\frac{zD}{\sqrt{x_D^2 + y_D^2}}\right).$$

A third spherical coordinate, r, given by:

$$\arg \min(\sqrt{(x_D-T_x^j)^2+(y_D-T_y^j)^2+(x_D-T_z^j)^2}) \tag{Eq.1}$$

defines the Euclidean distance between $S_i$ and the nearest voxel within T This conversion is repeated for each $S_i$ in S, yielding a 3D skeleton within the spherical coordinate space, $S_{ra\phi}$. $S_{ra\phi}$ is projected along each spherical dimension to yield the following 2D representations of 3D vessel orientation relative to the tumor centroid in spherical space: $V_{ra}^j$, azimuth angle with respect to the Euclidean distance from the tumor, illustrated at 128, $V_{r\phi}^j$, elevation angle with respect to the Euclidean distance from the tumor, illustrated at 126, and $V_{\alpha\phi}^j$, elevation angle with respect to azimuth angle, illustrated at 124.

Figure 6:
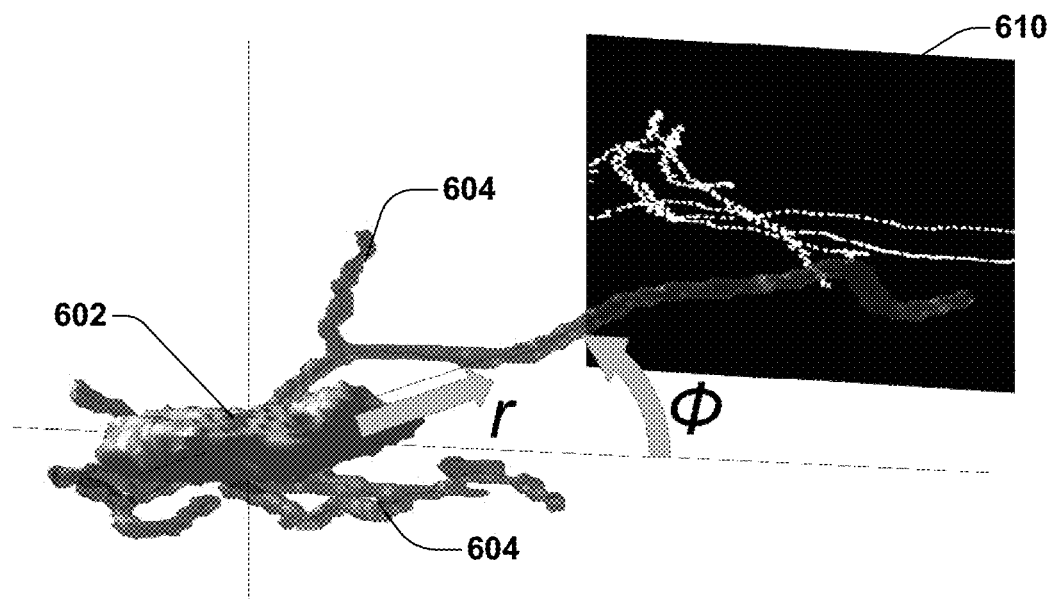
FIG. 6 illustrates a spherical vessel map.

FIG. 6 illustrates an example spherical vessel map. FIG. 6 includes a tumor 602 and a vasculature 604 associated with the tumor. FIG. 6 further illustrates a 2D representation 610 of vessel position of the vasculature 604 relative to the center and surface of tumor 602.

Embodiments compute sliding Hough transforms and aggregate peak orientations, as illustrated at 130. Embodiments compute and aggregate localized Hough transforms in the Cartesian space. Using a N×N sliding window W with an offset of k pixels, each pixel in $V_{xy}$ is mapped to an accumulator space using the Hough Transform, where the equation of a line is represented by y=(−cos θ/sin θ)x+(ρ/sin θ). This transforms the spatial coordinate system (x, y) to the polar coordinate system (ρ, θ), such that for every point on the medial axis representation $V_{xy}$, there exists a unique sinusoid in the Hough accumulator space, as illustrated at 132. These Hough domain representations depict the overlaid sinusoids for each point within the vasculature for the input representation, with θ along the x-axis and ρ along the y-axis. The five grid locations accumulating the most sinusoid crossings are identified for each W (depicted as regions of overlapping waveforms highlighted in red at 132). Feature set $F_{xy}$ then comprises the θ values associated with the five most prominent peak orientations such that $F_{xy}=[\theta_1, \theta_2, \ldots \theta_5]$.

Figure 7:
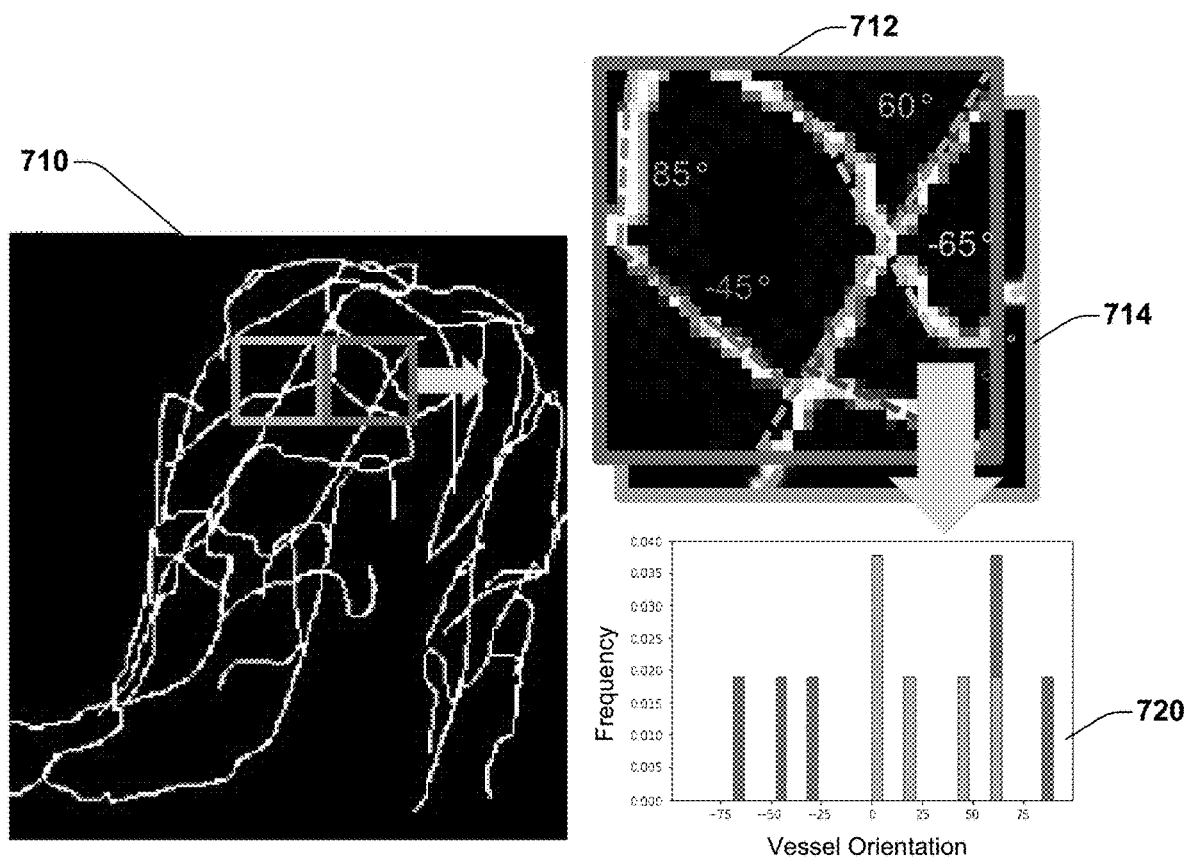
FIG. 7 illustrates a sliding window for analysis of local vessel orientation.

FIG. 7 illustrates an exemplary sliding window 710. Instances of vasculature captured by sliding window 710 are illustrated at 712 and 714. Graph 720 indicates frequency of vessel orientation as captured by the instances of sliding window 710 illustrated at 712 and 714.

Embodiments compute localized Hough transforms on spherical projections within annular sub-volumes. For a given annular sub-volume outside the tumor $I_N^j$, 2-D spherical representations are obtained from vessels only within the sub-volume, denoted as $V_{r\alpha}^j$, $V_{r\phi}^j$, and $V_{\alpha\phi}^j$. Peaks are computed from 2-D spherical representations using the above approach. This is repeated for all annular bands $j \in \{1, \ldots, k\}$. Peak orientations are concatenated for all annular bands, yielding a single feature vector, i.e. $F_{r\alpha} = [F_{r\alpha}^1, F_{r\alpha}^2, \ldots F_{r\alpha}^k]$, $F_{r\phi} = [F_{r\phi}^1, F_{r\phi}^2, \ldots F_{r\phi}^k]$, and $F_{\alpha\phi} = [F_{\alpha\phi}^1, F_{\alpha\phi}^2, \ldots F_{\alpha\phi}^k]$.

Embodiments compute a VaNgOGH descriptor. The final VaNgOGH feature set $F_v$ is a concatenation of the first order statistics, mean, median, standard deviation, skewness, and kurtosis of $F_{xy}$, $F_{r\alpha}$, $F_{r\phi}$, and $F_{\alpha\phi}$. In another embodiment, the final VaNgOGH feature set may include other, different features.

Figure 15:
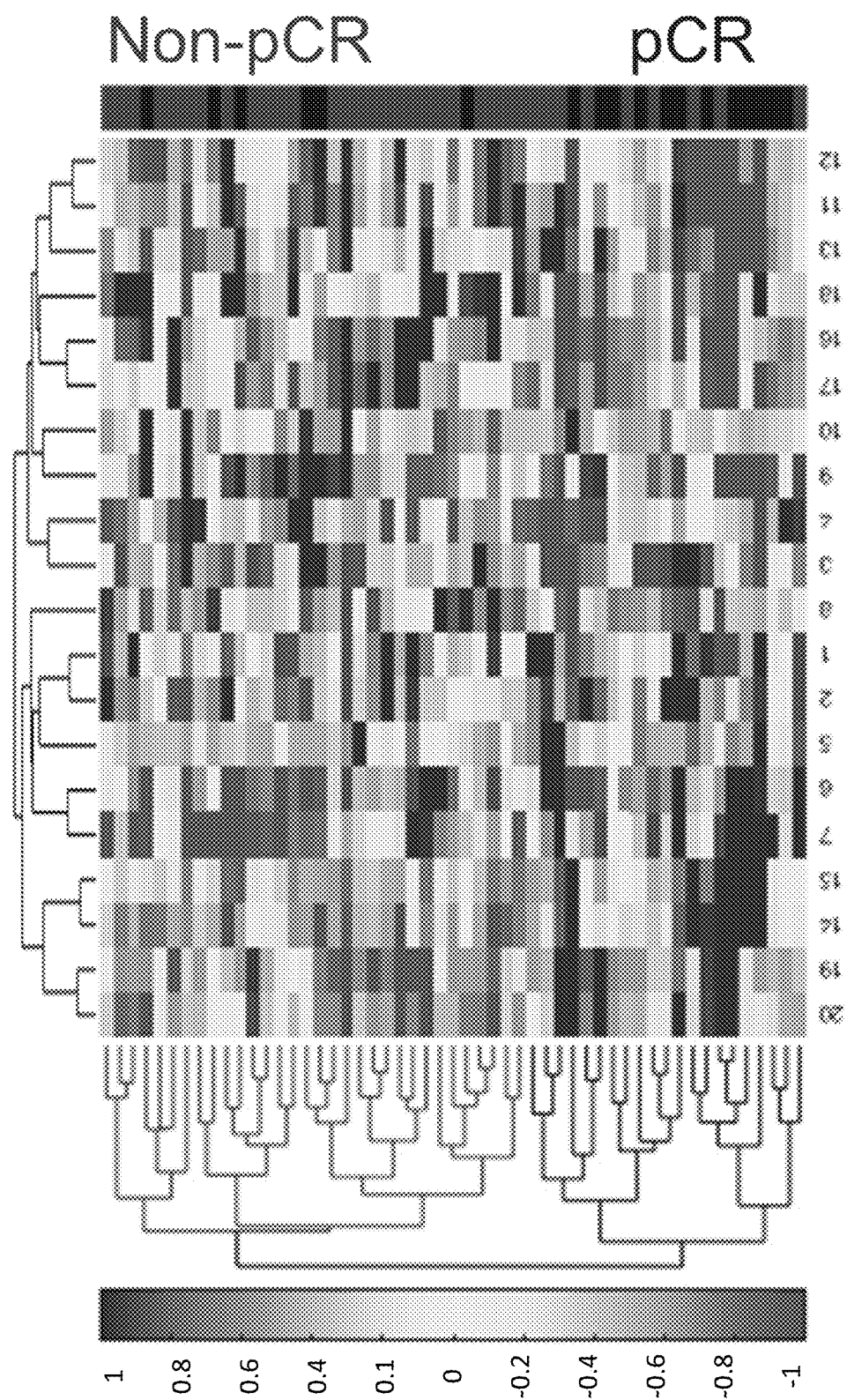
FIG. 15 illustrates results of unsupervised clustering of vascular network organization via Hough transform features.

Embodiments classify an ROI into a positive or negative class based on the VaNgOGH descriptor. Embodiments select, via a feature selection approach, the top most discriminative features for distinguishing positive from negative class members. In one embodiment, a Wilcoxon rank sum test feature selection approach is used to select the top four most discriminative features to train a machine learning classifier to distinguish positive from negative class members. In another embodiment, other feature selection techniques, including minimum redundancy, maximum relevance (mRMR) feature selection may be employed. In one embodiment, upon the extraction of the VaNgOGH features from a training set, a set of 4 top features is selected by Wilcoxon rank-sum test and used to train a linear discriminant analysis (LDA) classifier. The LDA classifier is trained and tested in a 3-fold cross-validation setting across 100 iterations. The locked-down model is then applied to an independent validation cohort. Performance of the LDA classifier is assessed by the area under the receiver operating characteristic curve (AUC) illustrated at 140. In one embodiment, unsupervised clustering techniques may be employed. FIG. 15 illustrates results of unsupervised clustering of VaNgOGH features in a training set, yielding response-associated groups (e.g., non-pCR, pCR).

In one embodiment, the ROI is an ROI demonstrating breast cancer (BCa) and embodiments classify the ROI as likely to experience pathological complete response (pCR) or unlikely to experience pCR (non-pCR) to chemotherapy on dynamic contrast enhanced magnetic resonance imaging (DCE-MRI) imagery. In this embodiment, a first dataset of pre-treatment imagery is accessed. The first dataset of pre-treatment imagery includes axial breast DCE-MRI imagery acquired with a 1.5 T/3 T magnet, collected prior to administration of neadjuvant chemotherapy. Embodiments derive subtraction images from MRI scans prior to, and immediately following contrast agent injection. Embodiments perform multi-scale vessel enhancement to emphasize the vasculature, which is then isolated by thresholding. A series of morphological operations are performed to remove noise and join adjacent vascular regions. Tumor boundaries are delineated. In one embodiment, automated segmentation techniques are employed to delineate a tumor boundary. In another embodiment, the tumor boundary may be delineated by an expert radiologist. Hough transforms are applied to image projections using a sliding window size, in one embodiment, of N=30 pixels with a step size k=5 pixels. Spherical projections are performed within annular sub-volumes with a radial width of 25 pixels out to a maximum radial distance of 100 pixels, with a step size=12.5 pixels. In another embodiment, other window sizes, step sizes, radial widths, or maximum radial distances may be employed.

Figure 2:
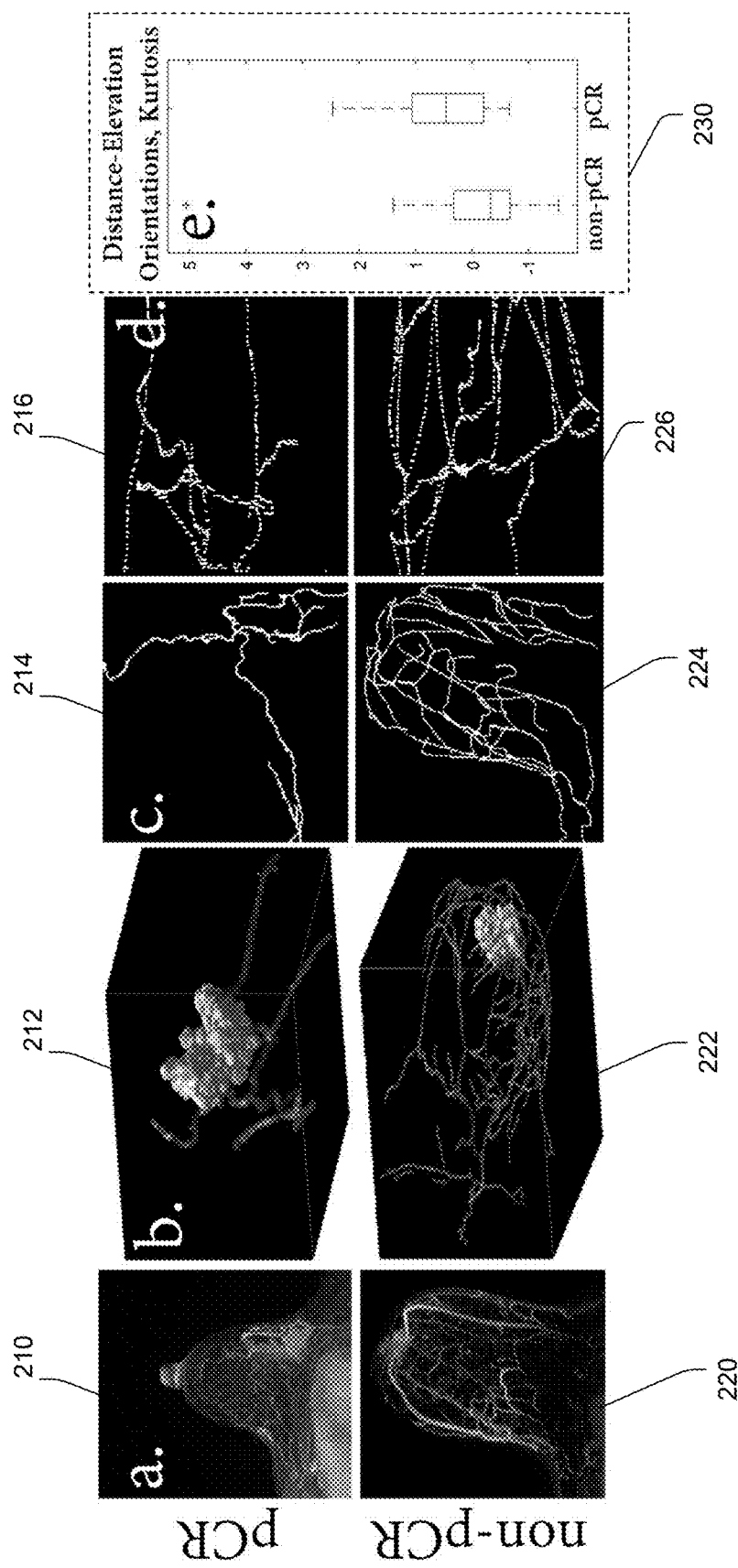
FIG. 2 illustrates differences in tumor vasculature in breast cancer (BCa) on dynamic contrast enhanced magnetic resonance imaging (DCE-MRI) imagery between a patient who achieved a pathological complete response (pCR) to chemotherapy and a non-responder (non-pCR).

FIG. 2 illustrates differences in tumor vascular networks from baseline DCE-MRI scans for two different BCa patients. Imagery of a patient who experienced pCR are illustrated at 210-216. Imagery of a patient who did not experience pCR are illustrated at 220-226. pCR demonstrates a less chaotic vascular network, illustrated by projection images 214 and 224 on the Cartesian plane and distance-elevation images at 216 and 226 on the spherical plane. Hough transformation on images 214 and 224 and 216 and 226 further accentuates the differences in vessel arrangement by detecting the orientation of straight line segments in the accumulator grid. In this example, the most discriminating VaNgOGH features include the standard deviation and kurtosis of $F_{\alpha\phi}$, and skewness and kurtosis of $F_{r\phi}$. Kurtosis of $F_{r\phi}$ is elevated in pCR, illustrated at boxplot 230, indicating a reduced disorder of vessel orientation in the $V_{r\phi}$ space.

In another embodiment, the ROI is an ROI of a region of tissue demonstrating lung nodules, and embodiments classify a lung nodule as a benign granuloma or as a malignant adenocarcinoma on non-contrast computed tomography (CT) imagery. Distinguishing granulomas from adenocarcinomas is amongst the most challenging clinical problems for lung radiologists, and embodiment provide the technical improvement of more accurate classification of lung nodules compared to existing approaches. In one embodiment, lung nodules are automatically segmented from non-lung nodule tissue using a watershed segmentation technique, region growing, an active contour technique, or a convolutional neural network (CNN). In another embodiment, nodules are manually segmented by a cardiothoracic radiologist. In one embodiment, to obtain the vasculature, lung regions are first isolated from the surrounding anatomy using a multi-threshold based algorithm. This is followed by region growing. The center of gravity of the segmented nodules may be used as the initial seed point for the region growing algorithm. Within the nodule volume, seed points are initialized at random locations. Based on the intensity similarity of the seed points and surrounding pixels, an initial region is iteratively grown to encompass the nodule and associated vasculature. VaNgOGH features are selected using a Wilcoxon rank sum test. Other feature selection techniques may be employed in other embodiments, including for example, an mRMR approach.

Figure 3:
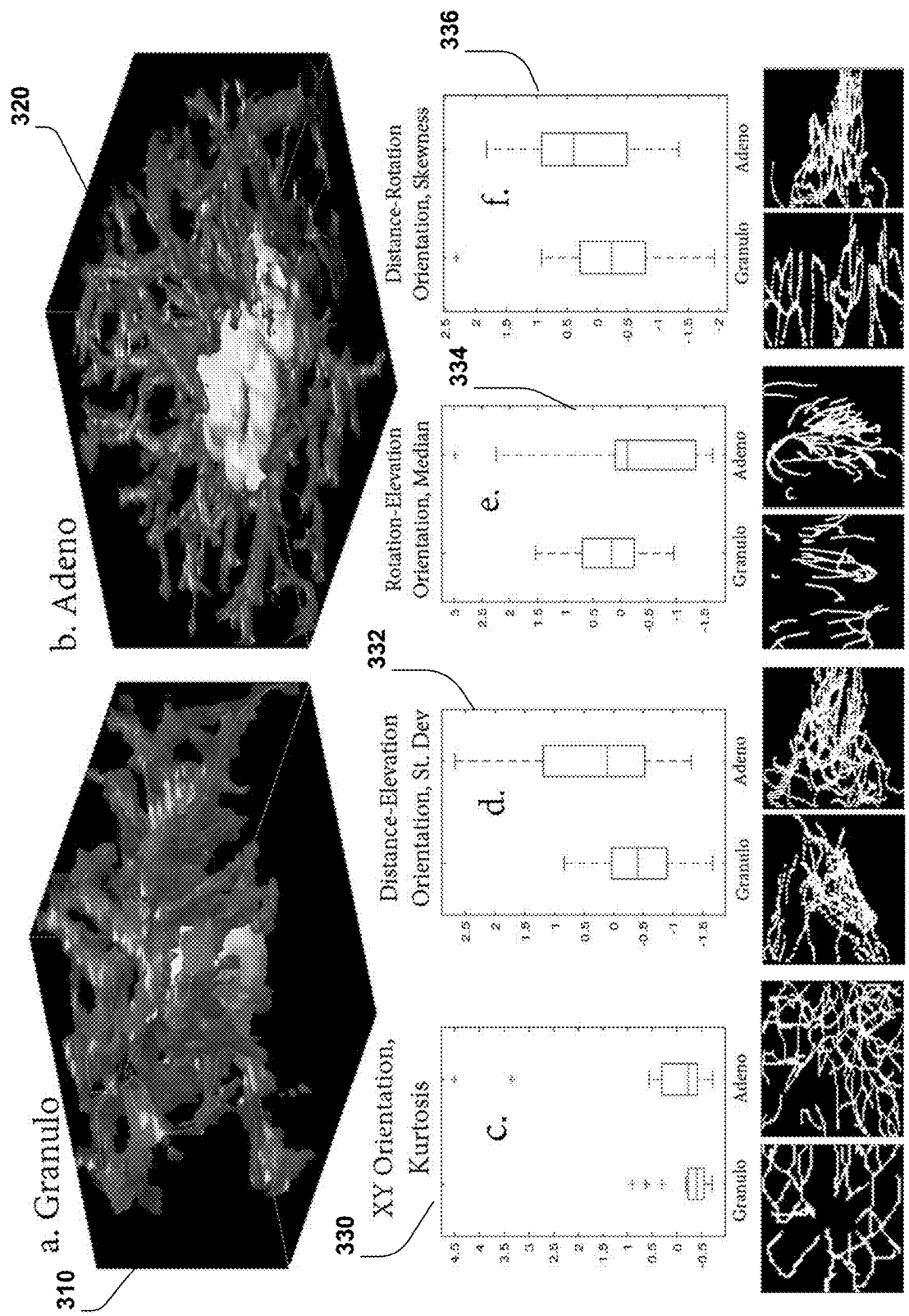
FIG. 3 illustrates differences in tumor vasculature between a granuloma and an adenocarcinoma on computed tomography (CT) imagery.

FIG. 3 illustrates similarly appearing granuloma and adenocarcinoma distinguished by embodiments. FIG. 3 illustrates at 310, vessel segmentation and centerlines for a granuloma. FIG. 3 also illustrates, at 320, vessel segmentation and centerlines for an adenocarcinoma. Boxplots 330-336 correspond to the top four most discriminative VaNgOGH features. Although both nodules are highly vascularized, spherical projections accentuate the elevated disorder of the vascular network in adenocarcinoma, whereas granuloma vessel orientations are predominantly linear in the $V_{\alpha\phi}$ space at 332, and the $V_{r\alpha}$ space at 334. Embodiments successfully separate adenocarcinomas and granulomas with an AUC of 0.65+−0.06. The top most discriminative feature set includes, in this example, one statistic for each view, including standard deviation of $F_{r\phi}$, median of $F_{\alpha\phi}$, kurtosis of $F_{xy}$, and skewness of $F_{r\alpha}$. FIG. 3 illustrates elevated vascular disorder in adenocarcinoma, indicated by the increased standard deviation of $F_{r\phi}$ at 332.

Embodiments quantify disorder of the tumor-associated vascular network in both BCa and in distinguishing granuloma from adenocarcinoma. Embodiments assess the morphology of vessel orientation across multiple spatial dimensions using the VaNgOGH descriptor. Embodiments predict benefit of neoadjuvant chemotherapy in BCa patients on DCE-MRI, and distinguish malignant adenocarcinoma from visually confounding granuloma on CT imagery. When combined with an existing radiomic response signature in breast MRI, embodiments further improve identification of patients who will experience pCR. For example, predicting pCR based on a VaNgOGH descriptor as described herein and further based on radiomic texture features extracted from the ROI, provides improved accuracy over existing approaches. For example, in one embodiment, a combination of VaNgOGH descriptor features with two intratumoral radiomic features (co-occurrence of local anisotropic gradient orientations entropy (CoLIAGe) Info1, Laws S5R5) and two peri-tumoral radiomic features (Laws L5S5, CoLIAGe Entropy) results in improved prediction of pCR compared to the existing radiomic approach that employs just the two intratumoral radiomic features and the two peri-tumoral radiomic features. In another embodiment, the predictions from a classifier utilizing VaNgOGH features is combined with predictions from a convolutional neural network (CNN), also resulting in an improvement in response prediction. In a further embodiment, predictions from all three of these tools: VaNgOGH, intra- and peri-tumoral texture features, and a CNN, may be combined to classify an ROI into a positive or negative class.

Some portions of the detailed descriptions herein are presented in terms of algorithms and symbolic representations of operations on data bits within a memory. These algorithmic descriptions and representations are used by those skilled in the art to convey the substance of their work to others. An algorithm, here and generally, is conceived to be a sequence of operations that produce a result. The operations may include physical manipulations of physical quantities. Usually, though not necessarily, the physical quantities take the form of electrical or magnetic signals capable of being stored, transferred, combined, compared, and otherwise manipulated in a logic or circuit, and so on. The physical manipulations create a concrete, tangible, useful, real-world result.

It has proven convenient at times, principally for reasons of common usage, to refer to these signals as bits, values, elements, symbols, characters, terms, numbers, and so on. It should be borne in mind, however, that these and similar terms are to be associated with the appropriate physical quantities and are merely convenient labels applied to these quantities. Unless specifically stated otherwise, it is appreciated that throughout the description, terms including processing, computing, calculating, determining, and so on, refer to actions and processes of a computer system, logic, circuit, processor, or similar electronic device that manipulates and transforms data represented as physical (electronic) quantities.

Example methods and operations may be better appreciated with reference to flow diagrams. While for purposes of simplicity of explanation, the illustrated methodologies are shown and described as a series of blocks, it is to be appreciated that the methodologies are not limited by the order of the blocks, as some blocks can occur in different orders and/or concurrently with other blocks from that shown and described. Moreover, less than all the illustrated blocks may be required to implement an example methodology. Blocks may be combined or separated into multiple components. Furthermore, additional and/or alternative methodologies can employ additional, not illustrated blocks.

Figure 8:
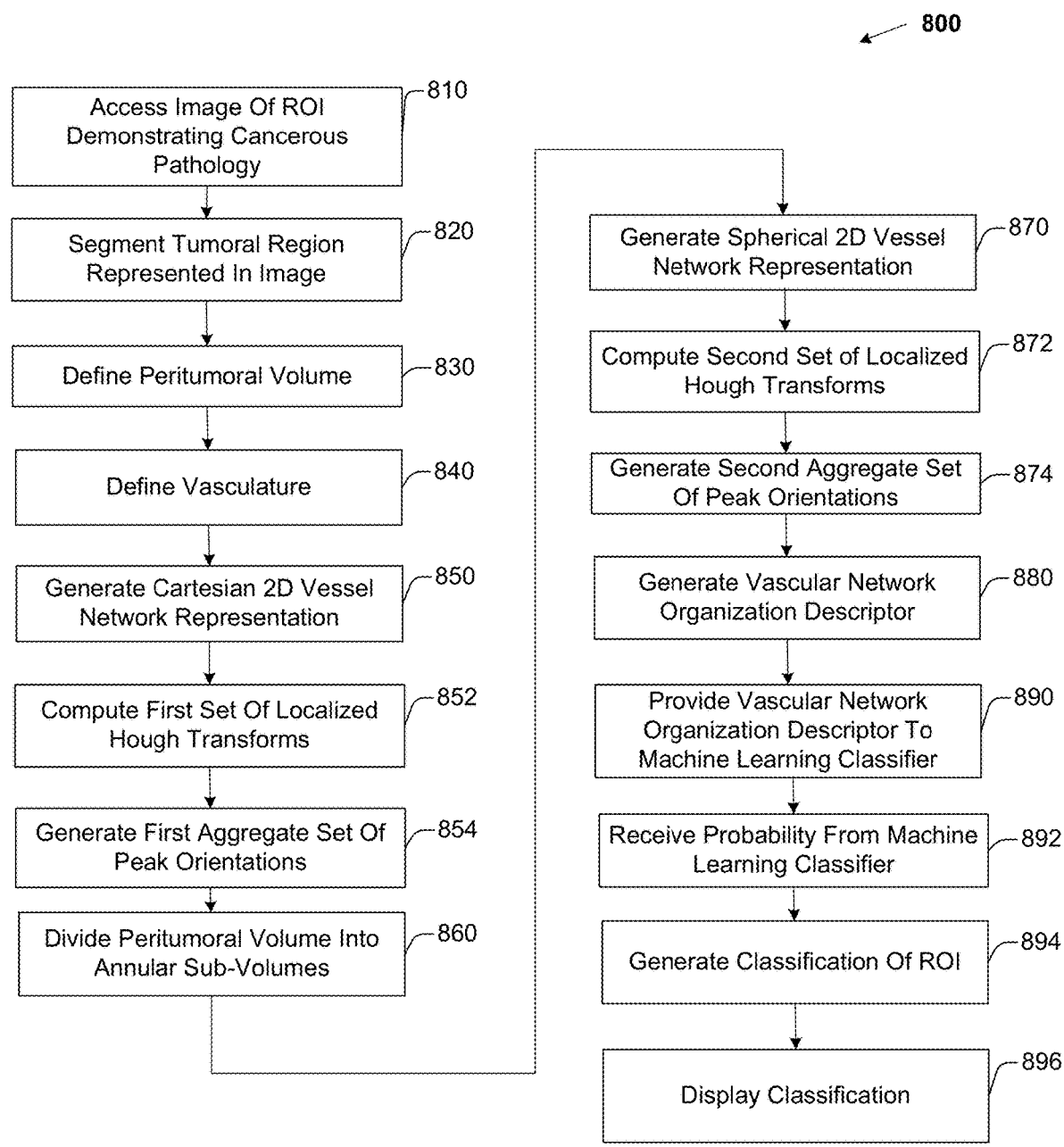
FIG. 8 is a flow diagram of example operations for distinguishing a positive class from a negative class based on the architectural disorder of a vascular architecture associated with a tumor or lesion.

FIG. 8 is a flow diagram of example operations 800 that may be performed by a processor for distinguishing a positive class from a negative class based on the architectural disorder of a vascular architecture associated with a tumor. A processor(s) may include any combination of general-purpose processors and dedicated processors (e.g., graphics processors, application processors, etc.). The processors may be coupled with or may include memory or storage and may be configured to execute instructions stored in the memory or storage to enable various apparatus, applications, or operating systems to perform the operations. The memory or storage devices may include main memory, disk storage, or any suitable combination thereof. The memory or storage devices may include, but are not limited to any type of volatile or non-volatile memory such as dynamic random access memory (DRAM), static random-access memory (SRAM), erasable programmable read-only memory (EPROM), electrically erasable programmable read-only memory (EEPROM), Flash memory, or solid-state storage.

The set of operations 800 includes, at 810, accessing a radiological image of a region of interest (ROI) of tissue demonstrating cancerous pathology. The radiological image has a plurality of voxels, a voxel having an intensity. The radiological image has a plane of acquisition z. The image includes a tumor and a peritumoral region. Accessing the image includes acquiring electronic data, reading from a computer file, receiving a computer file, reading from a computer memory, or other computerized activity not practically performed in a human mind. In one embodiment, the image is a DCE-MRI image of an ROI demonstrating breast cancer (BCa). In another embodiment, the image is a CT image of an ROI demonstrating lung nodules. In another embodiment, the image has other, different imaging parameters. While DCE-MRI images or CT images are described in this example, images acquired using other, different imaging modalities may be employed.

Operations 800 also includes, at 820, defining a tumoral volume by segmenting the tumor region represented in the image. The tumoral volume has a boundary and a centroid. In one embodiment, the tumoral region is segmented using a watershed segmentation technique, a region growing or active contour technique, or a convolutional neural network (CNN) approach. In another embodiment, the image includes a defined tumor volume having a boundary and a centroid, and thus step 820 may, in one embodiment, be skipped. Defining the tumoral volume includes acquiring electronic data, reading from a computer file, receiving a computer file, reading from a computer memory, or other computerized activity not practically performed in a human mind.

Operations 800 also includes, at 830, defining a peritumoral volume based on the boundary of the tumoral volume. In one embodiment, the peritumoral volume is defined by performing a morphological dilation of the tumoral boundary. A peritumoral region may be defined as the region surrounding the tumoral region out to a distance. For example, in one embodiment, the peritumoral region may be the region extending 20 mm from the tumoral boundary, or 100 pixels from the tumoral boundary. In another embodiment, the peritumoral region may be the region extending 10 mm, or 50 pixels from the tumoral boundary. The peritumoral region may be defined by a distance measured in mm, as described, or in other units, including pixels or voxels. In one embodiment, the peritumoral boundary may be defined as a function of a property of the tumor. The property of the tumor may include, for example, a diameter, a radius, a perimeter, an area, a volume, or other property of the tumor. The function may define the peritumoral region as, for example, a morphologic dilation of the tumoral boundary, where the dilation ratio is defined by a magnitude of an axis of the tumor. In another embodiment, the peritumoral boundary may be defined as a disc of a threshold radius defined about the centroid of the tumor, or defined on the focal points of an elliptical representation of the tumor. In one embodiment, the peritumoral boundary may be manually defined. Other approaches or combinations of approaches may be used to define the peritumoral boundary. Defining the peritumoral volume includes acquiring electronic data, reading from a computer file, receiving a computer file, reading from a computer memory, or other computerized activity not practically performed in a human mind.

Figure 14A:
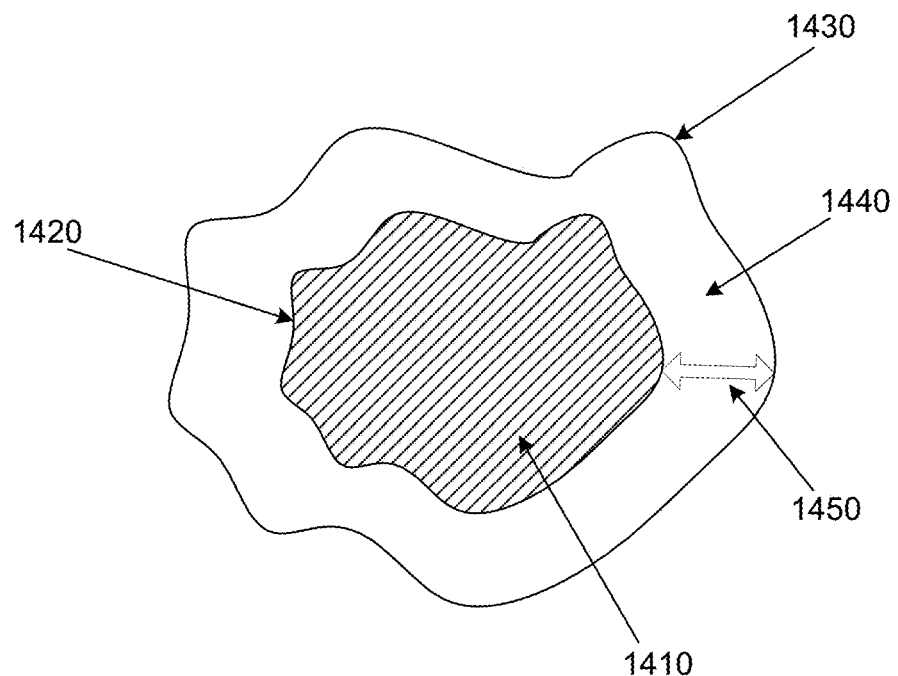
FIGS. 14A and 14B illustrate a tumoral region and a peritumoral region.
Figure 14B:
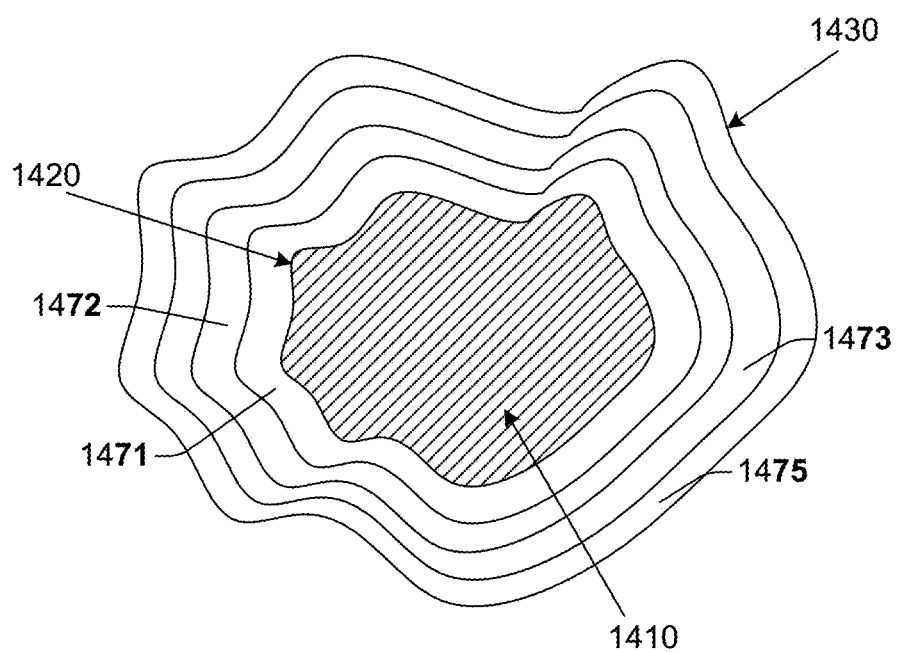

FIG. 14A illustrates an example tumoral region 1410. Tumoral region 1410 has a boundary 1420. A peritumoral region 1440 is defined by dilating the boundary 1420 a first amount 1450 (e.g., 100 pixels), generating a peritumoral boundary 1430. FIG. 14B illustrates annular rings 1471, 1472, 1473, and 1475.

Returning to FIG. 8, operations 800 also includes, at 840, defining a vasculature associated with the tumoral volume, where the vasculature is located within the peritumoral volume. In one embodiment, defining the vasculature includes: computing a centerline of a vessel of the vasculature; and generating a medial axis skeleton S of the vasculature, where S comprises a series of points in three dimensional (3D) Cartesian space. In this embodiment, generating the Cartesian 2D vessel network representation includes: projecting S along the plane of image acquisition z; and generating a 2D representation of S in the XY plane. Defining the vasculature includes acquiring electronic data, reading from a computer file, receiving a computer file, reading from a computer memory, or other computerized activity not practically performed in a human mind.

Operations 800 also includes, at 850, generating a Cartesian two-dimensional (2D) vessel network representation in the Cartesian domain based on the vasculature. In one embodiment, generating the Cartesian 2D vessel network representation includes: projecting S along the plane of image acquisition z; and generating a 2D representation of S in the XY plane. Generating the Cartesian 2D vessel network representation includes acquiring electronic data, reading from a computer file, receiving a computer file, reading from a computer memory, or other computerized activity not practically performed in a human mind.

Operations 800 also includes, at 852, computing a first set of localized Hough transforms based on the Cartesian 2D vessel network representation. In one embodiment, computing the first set of localized Hough transforms includes, for an N pixel by N pixel sliding window W with an offset of k pixels, mapping each pixel in the 2D representation of S in the XY plane to an accumulator space using a Hough transform to the 2D representation of S in the XY plane into polar co-ordinates ($\rho$, $\theta$), such that for each point in the medial axis skeleton S there exists a unique sinusoid in the accumulator space. Computing the first set of localized Hough transforms also includes identifying the top five grid locations accumulating the most sinusoid crossings for each window W Computing the first set of localized Hough transforms includes acquiring electronic data, reading from a computer file, receiving a computer file, reading from a computer memory, or other computerized activity not practically performed in a human mind.

Operations 800 also includes, at 854, generating a first aggregated set of peak orientations based on the first set of localized Hough transforms. In one embodiment, generating the first aggregated set of peak orientations based on the first set of localized Hough transforms includes: computing a feature set $F_{xy}$ comprising the $\theta$ values associated with the five most prominent peak orientations such that $F_{xy}=[\theta_1, \theta_2, \ldots \theta_5]$. Generating the first aggregated set of peak orientations includes acquiring electronic data, reading from a computer file, receiving a computer file, reading from a computer memory, or other computerized activity not practically performed in a human mind.

Operations 800 also includes, at 860, dividing the peritumoral volume into a set of annular sub-volumes. In one embodiment, an image scene I is defined as I=(C, f), where I is a spatial grid C of voxels c$\in$ C in a three-dimensional (3D) space $\mathbb{R}^3$. Each voxel, c$\in$ C, is associated with an intensity value f(c). $I_T$ and $I_P$ correspond to the intra-tumoral and surrounding peritumoral parenchyma sub-volumes within every I, respectively, such that $[I_T, I_P] \subset I$. Embodiments divide the sub-volume $I_P$ into uniformly sized annular sub-volumes IN, where j is the number of uniformly-sized annular bands, such that j$\in \{1, \ldots, k\}$, and k is a user-defined proximity parameter dependent on the distance g from the tumor margin. In another embodiment, other techniques may be employed to divide the peritumoral volume into a set of annular sub-volumes. Dividing the peritumoral volume into a set of annular sub-volumes includes acquiring electronic data, reading from a computer file, receiving a computer file, reading from a computer memory, or other computerized activity not practically performed in a human mind.

Operations 800 also includes, at 870, generating, for each annular sub-volume, respectively, a spherical 2D vessel network representation in the spherical domain based on the vasculature. In one embodiment, generating the spherical 2D vessel network representation includes: converting S into spherical coordinates; and generating three 2D representations of 3D vessel orientation with respect to the tumoral centroid by projecting S along each spherical dimension. Generating a spherical 2D vessel network representation in the spherical domain includes acquiring electronic data, reading from a computer file, receiving a computer file, reading from a computer memory, or other computerized activity not practically performed in a human mind.

Operations 800 also includes, at 872, computing a second, different set of localized Hough transforms and distribution of vessel orientations based on the spherical 2D vessel network representation of each annular sub-volume, respectively. In one embodiment, computing the second, different set of localized Hough transforms includes: computing peaks from the spherical 2D vessel network representation for each annular sub-volume. Computing the second, different set of localized Hough transforms includes acquiring electronic data, reading from a computer file, receiving a computer file, reading from a computer memory, or other computerized activity not practically performed in a human mind.

Operations 800 also includes, at 874, generating a second, different aggregated set of peak orientations based on the second set of localized Hough transforms. Generating the second, different aggregated set of peak orientations based on the second set of localized Hough transforms includes generating a feature vector by concatenating peak orientations for all the annular sub-volumes. Generating the second, different aggregated set of peak orientation includes acquiring electronic data, reading from a computer file, receiving a computer file, reading from a computer memory, or other computerized activity not practically performed in a human mind.

Operations 800 also includes, at 880, generating a vascular network organization descriptor based on the first aggregated set of peak orientations and the second aggregated set of peak orientations. In one embodiment, generating the vascular network organization descriptor comprises concatenating first order statistics of the first aggregated set of peak orientations and the second aggregated set of peak orientations. In one embodiment, the vascular network organization descriptor feature set is a set $F_v$ that is a concatenation of the first order statistics, mean, median, standard deviation, skewness, and kurtosis of $F_{xy}$, $F_{r\alpha}$, $F_{r\phi}$, $F_{\alpha\phi}$. Generating the vascular network organization descriptor (e.g., VaNgOGH descriptor) includes acquiring electronic data, reading from a computer file, receiving a computer file, reading from a computer memory, or other computerized activity not practically performed in a human mind.

Operations 800 also includes, at 890, providing the vascular network organization descriptor to a machine learning classifier configured to distinguish a positive class from a negative class. In one embodiment, the machine learning classifier is a linear discriminant analysis (LDA) classifier configured to distinguish a positive class from a negative class. In another embodiment, the machine learning classifier may be another type of machine learning classifier, including a support vector machine (SVM) classifier, a quadratic discriminant analysis (QDA) classifier, a random forest classifier, or a deep learning classifier, including a convolutional neural network (CNN). In one embodiment, the CNN is applied directly to 2D vessel representations. Providing the vascular network organization descriptor includes acquiring electronic data, reading from a computer file, receiving a computer file, reading from a computer memory, or other computerized activity not practically performed in a human mind.

Operations 800 also includes, at 892, receiving, from the machine learning classifier, a probability that the ROI is a member of the positive class. The machine learning classifier computes the probability based, at least in part, on the vascular network organization descriptor. The probability may, in one embodiment, include a value in the range [0, 1], for example, where a value of 1 indicates membership in the positive class, and a value of 0 indicates membership in the negative class. Other ranges may be employed. Receiving the probability includes acquiring electronic data, reading from a computer file, receiving a computer file, reading from a computer memory, or other computerized activity not practically performed in a human mind.

Operations 800 also includes, at 894, generating a classification of the ROI as a member of the positive class or the negative class based on the probability. For example, upon receiving a probability that is >0.5, the ROI may be classified as a member of the positive class. Upon receiving a probability of <=0.5, the ROI may be classified as a member of the negative class. Other classification schemes may be employed. For example, upon receiving a probability that is >=0.6, the ROI may be classified as a member of the positive class. Upon receiving a probability of <=0.4, the ROI may be classified as a member of the negative class, while upon receiving a probability that is >0.4 and <0.6, the ROI may be classified as, for example, "unknown". Generating the classification includes acquiring electronic data, reading from a computer file, receiving a computer file, reading from a computer memory, or other computerized activity not practically performed in a human mind.

Operations 800 further includes, at 896, displaying the classification. Displaying the classification may include displaying the classification on a computer monitor, a smartphone display, a tablet display, or other displays. Displaying the classification may also include printing the classification. Displaying the classification may also include controlling a pCR prediction system, a lung nodule classification system, a personalized medicine system, a computer assisted diagnostic (CADx), system a monitor, or other display, to display operating parameters or characteristics of a machine learning classifier, during both training and testing, or during clinical operation of the machine learning classifier. By displaying the classification, example embodiments provide a timely and intuitive way for a human pathologist or other medical practitioner to more accurately predict pCR in breast cancer, or to distinguish granuloma from adenocarcinoma, thus improving on existing approaches to predicting pCR in breast cancer, or for distinguishing granuloma from adenocarcinoma. The set of operations may further include, at 896, displaying the radiological image, the probability, the tumoral region, the vasculature, the peritumoral region, the Cartesian 2D vessel network representation in the Cartesian domain, a spherical 2D vessel network representation, an annular sub-volume, a first or second aggregated set of peak orientations, the vascular network organization descriptor.

In one embodiment, the radiological image is a dynamic-contrast enhanced magnetic resonance imaging (DCE-MRI) image of a region of tissue demonstrating breast cancer (BCa). In this embodiment, the positive class is tissue that will experience pathologic complete response (pCR) following neoadjuvant chemotherapy (NAC), and the negative class is tissue that will not experience pCR following NAC. In this embodiment, the LDA classifier is trained to distinguish tissue that will experience pCR from tissue that will not experience pCR in DCE-MRI imagery.

In one embodiment, the radiological image is a computed tomography (CT) image of a region of tissue demonstrating lung nodules. In this embodiment, the positive class is adenocarcinoma, and the negative class is granuloma. In this embodiment, the LDA classifier is trained to distinguish granuloma from adenocarcinoma in CT imagery.

Figure 9:
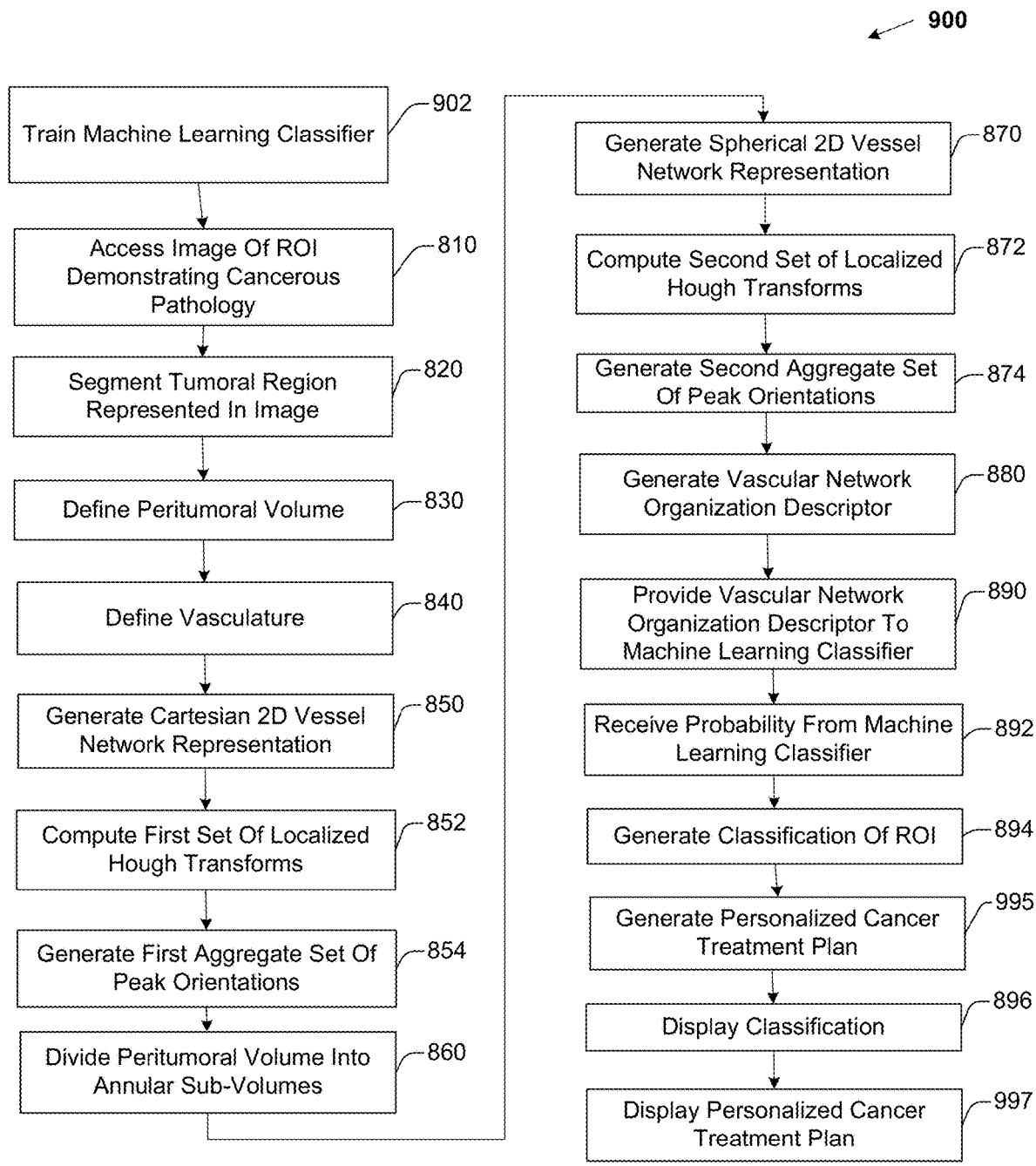
FIG. 9 is a flow diagram of example operations for distinguishing a positive class from a negative class based on the architectural disorder of a vascular architecture associated with a tumor or lesion.

In one embodiment, the operations may further include training the machine learning classifier. FIG. 9 is a flow diagram of example operations 900 that is similar to operations 800 but that includes additional details and elements. In this embodiment, operations 900 include, at 902, training the machine learning classifier. The machine learning classifier is trained and tested using a training set of images and a testing set of images. Training the machine learning classifier may include training the machine learning classifier until a threshold level of accuracy is achieved, until a threshold time has been spent training the machine learning classifier, until a threshold amount of computational resources have been expended training the machine learning classifier, or until a user terminates training. Other training termination conditions may be employed. Training the machine learning classifier may also include determining which vascular network organization descriptor is most discriminative in distinguishing a positive class from a negative class (e.g., pCR vs. non-pCR, granuloma vs. adenocarcinoma) or determining the optimal combination of parameters used in the computation of vascular network organization descriptors (e.g. size and stride of the sliding Hough window, maximum peri-tumoral radius to include, or size and number of annular subregions analyzed) to best separate a positive and negative class.

Embodiments may further include generating a personalized cancer treatment plan. Operations 900 also includes, at 995, generating a personalized cancer treatment plan based, at least in part, on the classification. For example, operations 900 may include, at 995 computing a first dosage or dosage schedule of a first immunotherapy agent based, at least in part, on the classification when the ROI is classified as a member of the positive class, or a second dosage or dosage schedule of a second, different immunotherapy agent based, at least in part, on the classification when the ROI is classified as a member of the negative class. For example, for a region of tissue demonstrating BCa classified as likely to experience pCR, a first dosage schedule may be generated, while for a region of tissue classified as unlikely to experience pCR, a second, different dosage schedule of a different immunotherapy agent may be generated. In another example, for a region of tissue demonstrating lung nodules classified as granuloma, a first treatment plan may be generated, while for a region of tissue demonstrating lung nodules classified as adenocarcinoma, a second, different treatment plan may be generated. Different personalized treatment plans may also generate different follow-up or monitoring schedules depending on the classification. For example, a lung nodule classified as adenocarcinoma may be scheduled, according to the personalized cancer treatment plan, more frequent monitoring, than a nodule classified as granuloma. In this embodiment, operations 900 further include at 997, displaying the personalized cancer treatment plan.

While FIGS. 8 and 9 illustrate various actions occurring in serial, it is to be appreciated that various actions illustrated in FIG. 8 or FIG. 9 could occur substantially in parallel. By way of illustration, a first process could involve generating a Cartesian 2D vessel network representation, a second process could involve generating a spherical 2D vessel network representation, and a third process could involve computing a Hough transform. While three processes are described, it is to be appreciated that a greater or lesser number of processes could be employed and that lightweight processes, regular processes, threads, and other approaches could be employed.

In one example, a method may be implemented as computer executable instructions. Thus, in one example, a computer-readable storage device may store computer executable instructions that if executed by a machine (e.g., computer, processor) cause the machine to perform methods or operations described or claimed herein including operations 800 or 900, method 1300, or any other methods or operations described herein. While executable instructions associated with the listed methods are described as being stored on a computer-readable storage device, it is to be appreciated that executable instructions associated with other example methods or operations described or claimed herein may also be stored on a computer-readable storage device. In different embodiments the example methods or operations described herein may be triggered in different ways. In one embodiment, a method or operation may be triggered manually by a user. In another example, a method or operation may be triggered automatically.

Improved identification of responders or non-responders to NAC in BCa, or improved classification of a lung nodule as granuloma or adenocarcinoma, based on a vascular network organization descriptor as described herein, may produce the technical effect of improving the administration of BCa treatments, by increasing the accuracy of and decreasing the time required to determine if a patient is likely to experience pCR. Treatments and resources, including expensive immunotherapy agents or chemotherapy may be more accurately tailored to patients with a likelihood of benefiting from said treatments and resources, including responding to immunotherapy or chemotherapy, so that more appropriate treatment protocols may be employed, and expensive resources are not wasted, when ROIs represented in digitized radiological images are more accurately and more quickly classified. For example, patients identified as having granuloma rather than adenocarcinoma may be spared treatment or surgical procedures. Controlling a BCa pCR prediction apparatus, a lung nodule classification apparatus, a CADx system, a personalized medicine system, or other apparatus configured to predict pCR in BCa or distinguish granuloma from adenocarcinoma on lung CT imagery, based on improved, more accurate analysis of digitized radiological images further improves the operation of the system, processor, or apparatus, since the accuracy of the system, processor, or apparatus is increased and unnecessary operations will not be performed.

Embodiments described herein, including at least operations 800 and 900, apparatus 1000 or 1100, or method 1300, resolve features extracted from digitized radiological images imagery at a higher order or higher level than a human can resolve in the human mind or with pencil and paper. For example, 3D vascular features in the spherical domain that are not perceivable by the human eye may be detected by embodiments, and 2D projections of 3D vasculatures generated by embodiments are not properties of a tissue that are perceivable by the human eye, computable using pencil and paper, or practically computed in the human mind. Embodiments thus perform actions, steps, processes, or other actions that are not practically performed in the human mind, at least because they require a processor or circuitry to access digitized images stored in a computer memory and to extract or compute features including the generation of vascular features in Cartesian or spherical co-ordinates that are based on the digitized images and not on properties of tissue or the images that are perceivable by the human eye. Embodiments described herein use a combined order of specific rules, elements, operations, or components that render information into a specific format that is then used and applied to create desired results more accurately, more consistently, and with greater reliability than existing approaches, thereby producing the technical effect of improving the performance of the machine, computer, or system with which embodiments are implemented.

Figure 10:
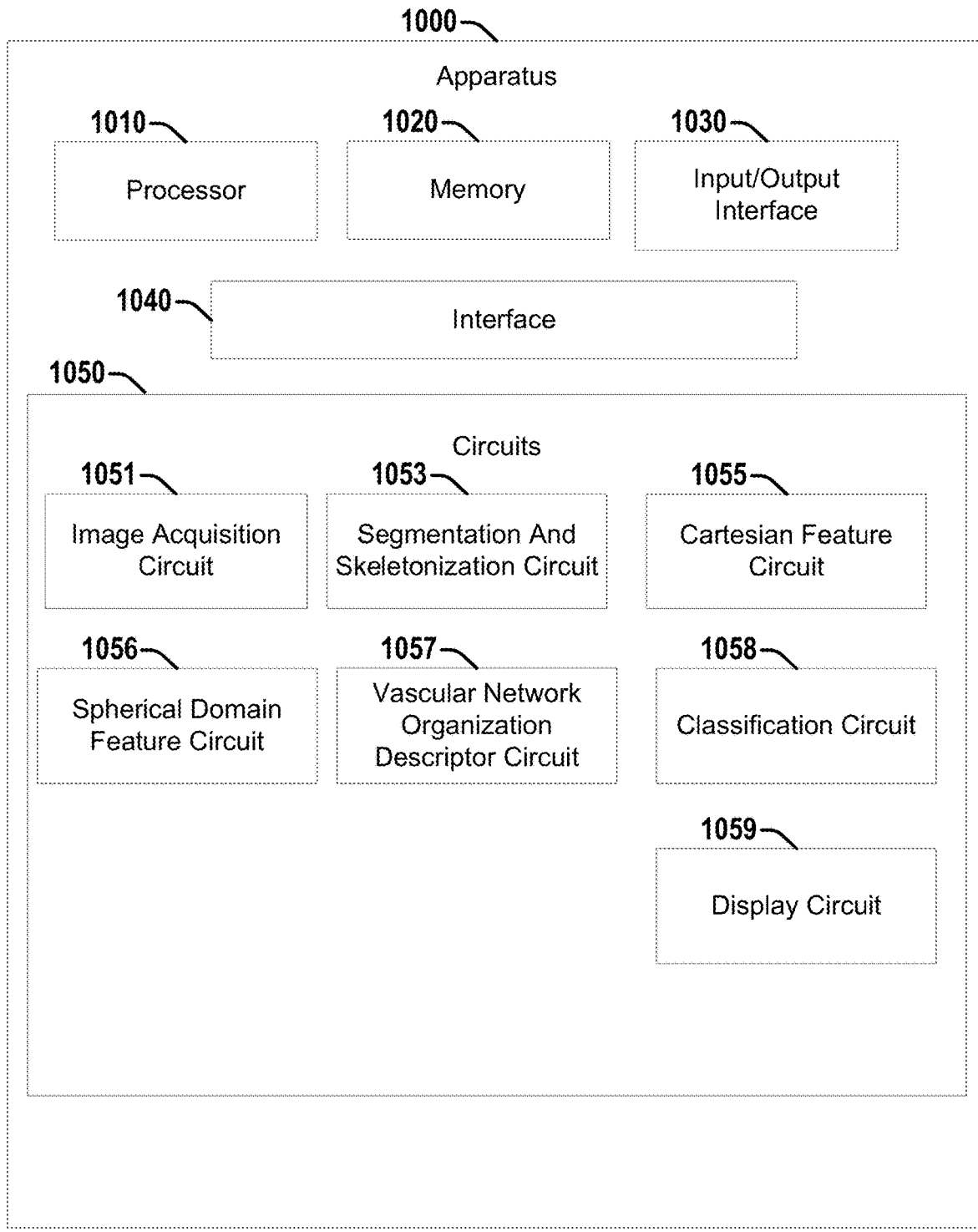
FIG. 10 illustrates an example apparatus for distinguishing a positive class from a negative class based on the architectural disorder of a vascular architecture associated with a tumor or lesion.

FIG. 10 illustrates an example apparatus 1000. Apparatus 1000 may be configured to generate a radiomic descriptor of tumor vascular morphology and classify a region of tissue into a positive class or a negative class based on the descriptor. Apparatus 1000 includes a processor 1010. Apparatus 1000 also includes a memory 1020. Processor 1010 may, in one embodiment, include circuitry such as, but not limited to, one or more single-core or multi-core processors. Processor 1010 may include any combination of general-purpose processors and dedicated processors (e.g., graphics processors, application processors, etc.). The processors may be coupled with or may include memory (e.g. memory 1020) or storage and may be configured to execute instructions stored in the memory 1020 or storage to enable various apparatus, applications, or operating systems to perform the operations. Memory 1020 is configured to store a digitized image of a region of interest (ROI) demonstrating cancerous pathology. The digitized image has a plurality of voxels, a voxel having an intensity.

Memory 1020 may be further configured to store a first training set of images demonstrating cancerous pathology, or a first testing set of images demonstrating cancerous pathology. At least one member of the first training set is classified as likely to experience pCR, and at least one other, different member of the first training set is classified as unlikely to experience pCR. At least one member of the first testing set is classified as likely to experience pCR, and at least one other, different member of the first testing set is classified as unlikely to experience pCR. Memory 1020 may be further configured to store a second training set of images demonstrating cancerous pathology, where at least one member of the second training set is classified as granuloma, and at least one other, different member of the second training set is classified as adenocarcinoma, or a second testing set of images demonstrating cancerous pathology, where at least one member of the second testing set is classified as granuloma, and at least one other, different member of the second testing set is classified as adenocarcinoma. In another embodiment, a training set or a testing set may include radiological image of other, different positive and negative classes.

Apparatus 1000 also includes an input/output (I/O) interface 1030, a set of circuits 1050, and an interface 1040 that connects the processor 1010, the memory 1020, the I/O interface 1030, and the set of circuits 1050. I/O interface 1030 may be configured to transfer data between memory v20, processor 1010, circuits 1050, and external devices, for example, a BCa pCR prediction system, a lung nodule classification system, a CADx system, an MRI system, a CT system, or a digital whole slide scanner.

The set of circuits 1050 includes an image acquisition circuit 1051. Image acquisition circuit 1051 is configured to access a digitized radiological image of a region of interest. The ROI includes a tumor and a peritumoral region. The digitized radiological image has a plurality of voxels, a voxel having an intensity. The image has a plane of acquisition z. Accessing the digitized image may include accessing a digitized image stored in memory 1020. In one embodiment, accessing the digitized image may include accessing a digitized image stored in a data storage device, including a hard disk drive, a solid state device, a tape drive, or accessing a digitized image over a local area network. Accessing the digitized image includes acquiring electronic data, reading from a computer file, receiving a computer file, reading from a computer memory, or other computerized activity not practically performed in a human mind.

The set of circuits 1050 also includes a segmentation and skeletonization circuit 1053. Segmentation and skeletonization circuit 1053 is configured to define a tumoral volume by segmenting the tumor region represented in the image. The tumoral volume has a boundary and a centroid. Segmentation and skeletonization circuit 1053 is also configured to define a peritumoral volume based on the boundary of the tumoral volume. Segmentation and skeletonization circuit 1053 is further configured to define a vasculature associated with the tumoral volume. The vasculature is located within the peritumoral volume.

The set of circuits 1050 also includes a Cartesian feature circuit 1055 configured to generate a Cartesian two-dimensional (2D) vessel network representation in the Cartesian domain based on the vasculature. Cartesian feature circuit 1055 is also configured to compute a first set of localized Hough transforms based on the Cartesian 2D vessel network representation. Cartesian feature circuit 1055 is further configured to generate a first aggregated set of peak orientations based on the first set of localized Hough transforms.

The set of circuits 1050 also includes a spherical domain feature circuit 1056 configured to divide the peritumoral volume into a set of annular sub-volumes. Spherical domain feature circuit 1056 is also configured to generate, for each annular sub-volume, respectively, a spherical 2D vessel network representation in the spherical domain based on the vasculature. Spherical domain feature circuit 1056 is also configured to compute a second, different set of localized Hough transforms based on the spherical 2D vessel network representation of each annular sub-volume, respectively. Spherical domain feature circuit 1056 is further configured to generate a second, different aggregated set of peak orientations based on the second set of localized Hough transforms.

The set of circuits 1050 also includes a vascular network organization descriptor circuit 1057 configured to generate a vascular network organization descriptor. Vascular network organization circuit 1057 is configured to generate the vascular network organization descriptor based on the first aggregated set of peak orientations and the second aggregated set of peak orientations.

The set of circuits 1050 also includes a classification circuit 1058 configured to compute a probability that the ROI is a member of a positive class or negative class. Classification circuit 1058 is configured to compute the probability based, at least in part, on the vascular network organization descriptor. In one embodiment, classification circuit 1058 is configured as a linear discriminant analysis (LDA) classifier. In another embodiment, classification circuit 1058 may be configured as another, different type of machine learning classifier or deep learning classifier, including, for example, a QDA classifier, a random forests classifier, or as a CNN classifier. Classification circuit 1058 is further configured to generate a classification of the ROI as a member of the positive class or the negative class based on the probability.

The set of circuits 1050 further includes a display circuit 1059 configured to display the classification. In one embodiment, display circuit 1059 is further configured to display at least one of the radiological image, the tumoral volume, the peritumoral volume, the vasculature, the Cartesian 2D vessel network representation, the first set of localized Hough transforms, the first aggregated set of peak orientations, an annular sub-volume, a spherical 2D vessel network representation, a second set of localized Hough transforms, a second aggregated set of peak orientations, a vascular network organization descriptor, or the probability. Displaying the classification or at least one of the radiological image, the tumoral volume, the peritumoral volume, the vasculature, the Cartesian 2D vessel network representation, the first set of localized Hough transforms, the first aggregated set of peak orientations, an annular sub-volume, a spherical 2D vessel network representation, a second set of localized Hough transforms, a second aggregated set of peak orientations, a vascular network organization descriptor, or the probability may also include printing the classification or at least one of the radiological image, the tumoral volume, the peritumoral volume, the vasculature, the Cartesian 2D vessel network representation, the first set of localized Hough transforms, the first aggregated set of peak orientations, an annular sub-volume, a spherical 2D vessel network representation, a second set of localized Hough transforms, a second aggregated set of peak orientations, a vascular network organization descriptor, or the probability.

In one embodiment, the digitized radiological image of an ROI is a DCE-MRI image of a region of tissue demonstrating BCa. In this embodiment, the positive class is tissue that will experience pathologic complete response (pCR) following neoadjuvant chemotherapy (NAC), and the negative class is tissue that will not experience pCR following NAC.

In one embodiment, the digitized radiological image of an ROI is a CT image of a region of tissue demonstrating lung nodules. In this embodiment, the positive class is adenocarcinoma, and the negative class is granuloma.

Figure 11:
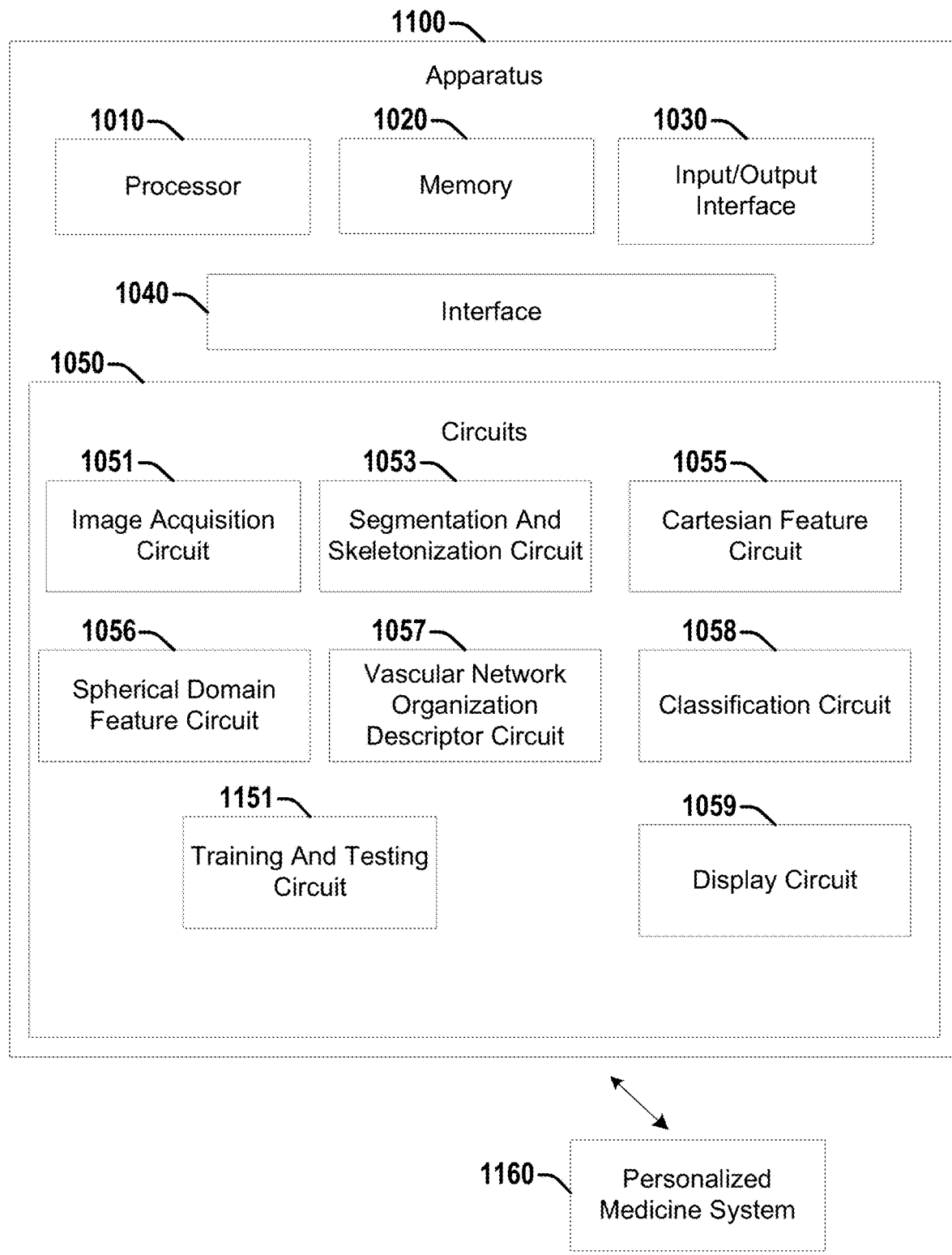
FIG. 11 illustrates an example apparatus for distinguishing a positive class from a negative class based on the architectural disorder of a vascular architecture associated with a tumor or lesion.

In one embodiment, apparatus 1000 may also include a training circuit. FIG. 11 illustrates an embodiment of apparatus 1100 that is similar to apparatus 1000 but that includes additional elements and details. Apparatus 1100 includes training and testing circuit 1151. The training and testing circuit 1151 may be configured to train a machine learning classifier (e.g., classification circuit 1058) to compute a probability that the ROI is a member of a positive class according to techniques described herein. In one embodiment, training and testing circuit 1151 is configured to access a training dataset of digitized images. The training and testing circuit 1151 may be further configured to access a testing dataset of digitized images. At least one member of the training set is classified as a member of the positive class, and at least one other, different member of the training set is classified as a member of the negative class. At least one member of the testing set is classified as a member of the positive class, and at least one other, different member of the testing set is classified as a member of the negative class. Training the machine learning classifier may include training the machine learning classifier until a threshold level of accuracy is achieved, until a threshold time has been spent training the machine learning classifier, until a threshold amount of computational resources have been expended training the machine learning classifier, or until a user terminates training. Other training termination conditions may be employed.

Apparatus 1100 may be configured to transmit the classification, the radiological image, the tumoral volume, the peritumoral volume, the vasculature, the Cartesian 2D vessel network representation, the first set of localized Hough transforms, the first aggregated set of peak orientations, an annular sub-volume, a spherical 2D vessel network representation, a second set of localized Hough transforms, a second aggregated set of peak orientations, a vascular network organization descriptor, or the probability or other information to personalized medicine system 1160. Apparatus 1100 may be configured to control personalized medicine system 1160 to display at least one of the classification, the radiological image, the tumoral volume, the peritumoral volume, the vasculature, the Cartesian 2D vessel network representation, the first set of localized Hough transforms, the first aggregated set of peak orientations, an annular sub-volume, a spherical 2D vessel network representation, a second set of localized Hough transforms, a second aggregated set of peak orientations, a vascular network organization descriptor, or the probability or other information. In one embodiment, personalized medicine system 1160 may be configured as a member of circuits 1050.

Personalized medicine system 1160 may be configured to generate a personalized cancer treatment plan based, at least in part, on the classification. For example, personalized medicine system 1160 may be configured to compute a first dosage or dosage schedule of a first immunotherapy agent based, at least in part, on the classification when the ROI is classified as a member of the positive class, or a second dosage or dosage schedule of a second, different immunotherapy agent based, at least in part, on the classification when the ROI is classified as a member of the negative class. For example, for a region of tissue demonstrating BCa classified as likely to experience pCR, a first dosage schedule may be generated, while for a region of tissue classified as unlikely to experience pCR, a second, different dosage schedule of a different immunotherapy agent may be generated. In another example, for a region of tissue demonstrating lung nodules classified as granuloma, a treatment plan may be generated, while for a region of tissue demonstrating lung nodules classified as adenocarcinoma, a second, different treatment plan may be generated. Different personalized treatment plans may also generate different follow-up or monitoring schedules depending on the classification. For example, a lung nodule classified as adenocarcinoma may be scheduled, according to the personalized cancer treatment plan, more frequent monitoring, than a nodule classified as granuloma.

Figure 12:
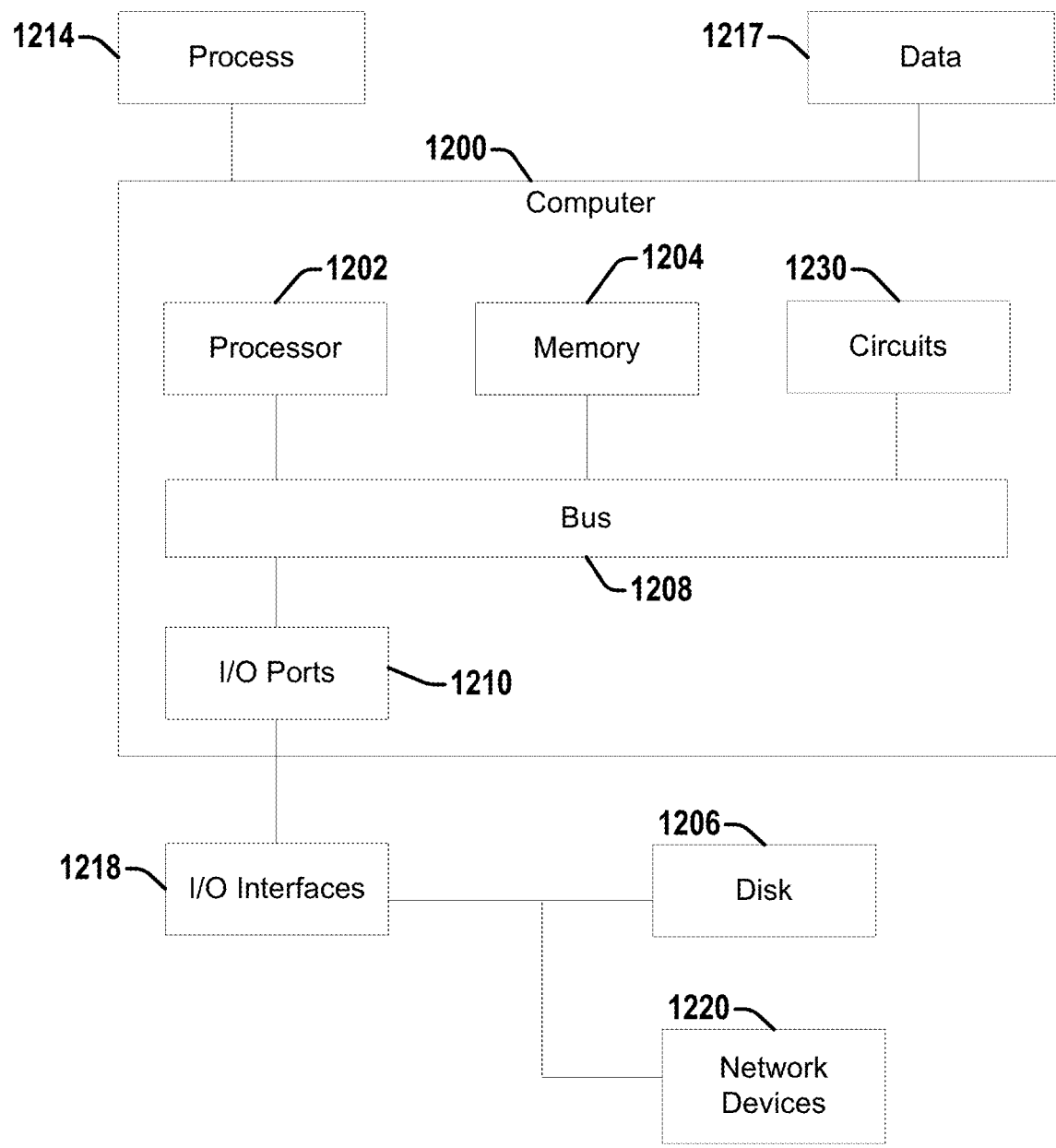
FIG. 12 illustrates an example computer in which embodiments described herein may operate.

FIG. 12 illustrates an example computer 1200 in which example methods illustrated herein can operate and in which example methods, apparatus, circuits, operations, or logics may be implemented. In different examples, computer 1200 may be part of a BCa pCR prediction system or apparatus, a lung nodule classification system or apparatus, a CADx system, an MRI system, a CT system, a digital whole slide scanner, or a personalized medicine system, or may be operably connectable to a BCa pCR prediction system or apparatus, a lung nodule classification system or apparatus, a CADx system, an MRI system, a CT system, a digital whole slide scanner, or a personalized medicine system.

Computer 1200 includes a processor 1202, a memory 1204, and input/output (I/O) ports 1210 operably connected by a bus 1208. In one example, computer 1200 may include a set of logics or circuits 1230 that perform operations for or a method of predicting pCR in BCa, or classifying lung nodules on CT imagery, including by using a machine learning classifier. Thus, the set of circuits 1230, whether implemented in computer 1200 as hardware, firmware, software, and/or a combination thereof may provide means (e.g., hardware, firmware, circuits) for predicting pCR in BCa, or classifying lung nodules on CT imagery. In different examples, the set of circuits 1230 may be permanently and/or removably attached to computer 1200.

Processor 1202 can be a variety of various processors including dual microprocessor and other multi-processor architectures. Processor 1202 may be configured to perform steps of methods claimed and described herein. Memory 1204 can include volatile memory and/or non-volatile memory. A disk 1206 may be operably connected to computer 1200 via, for example, an input/output interface (e.g., card, device) 1218 and an input/output port 1210. Disk 1206 may include, but is not limited to, devices like a magnetic disk drive, a tape drive, a Zip drive, a flash memory card, or a memory stick. Furthermore, disk 1206 may include optical drives like a CD-ROM or a digital video ROM drive (DVD ROM). Memory 1204 can store processes 1214 or data 1217, for example. Data 1217 may, in one embodiment, include digitized radiological images, including DCE-MRI images of tissue demonstrating BCa, or CT imagery of lung nodules. Disk 1206 or memory 1204 can store an operating system that controls and allocates resources of computer 1200.

Bus 1208 can be a single internal bus interconnect architecture or other bus or mesh architectures. While a single bus is illustrated, it is to be appreciated that computer 1200 may communicate with various devices, circuits, logics, and peripherals using other buses that are not illustrated (e.g., PCIE, SATA, Infiniband, 1394, USB, Ethernet).

Computer 1200 may interact with input/output devices via I/O interfaces 1218 and input/output ports 1210. Input/output devices can include, but are not limited to, CT systems, MRI systems, digital whole slide scanners, an optical microscope, a keyboard, a microphone, a pointing and selection device, cameras, video cards, displays, disk 1206, network devices 1220, or other devices. Input/output ports 1210 can include but are not limited to, serial ports, parallel ports, or USB ports.

Computer 1200 may operate in a network environment and thus may be connected to network devices 1220 via I/O interfaces 1218 or I/O ports 1210. Through the network devices 1220, computer 1200 may interact with a network. Through the network, computer 1200 may be logically connected to remote computers. The networks with which computer 1200 may interact include, but are not limited to, a local area network (LAN), a wide area network (WAN), or other networks, including the cloud.

Figure 13:
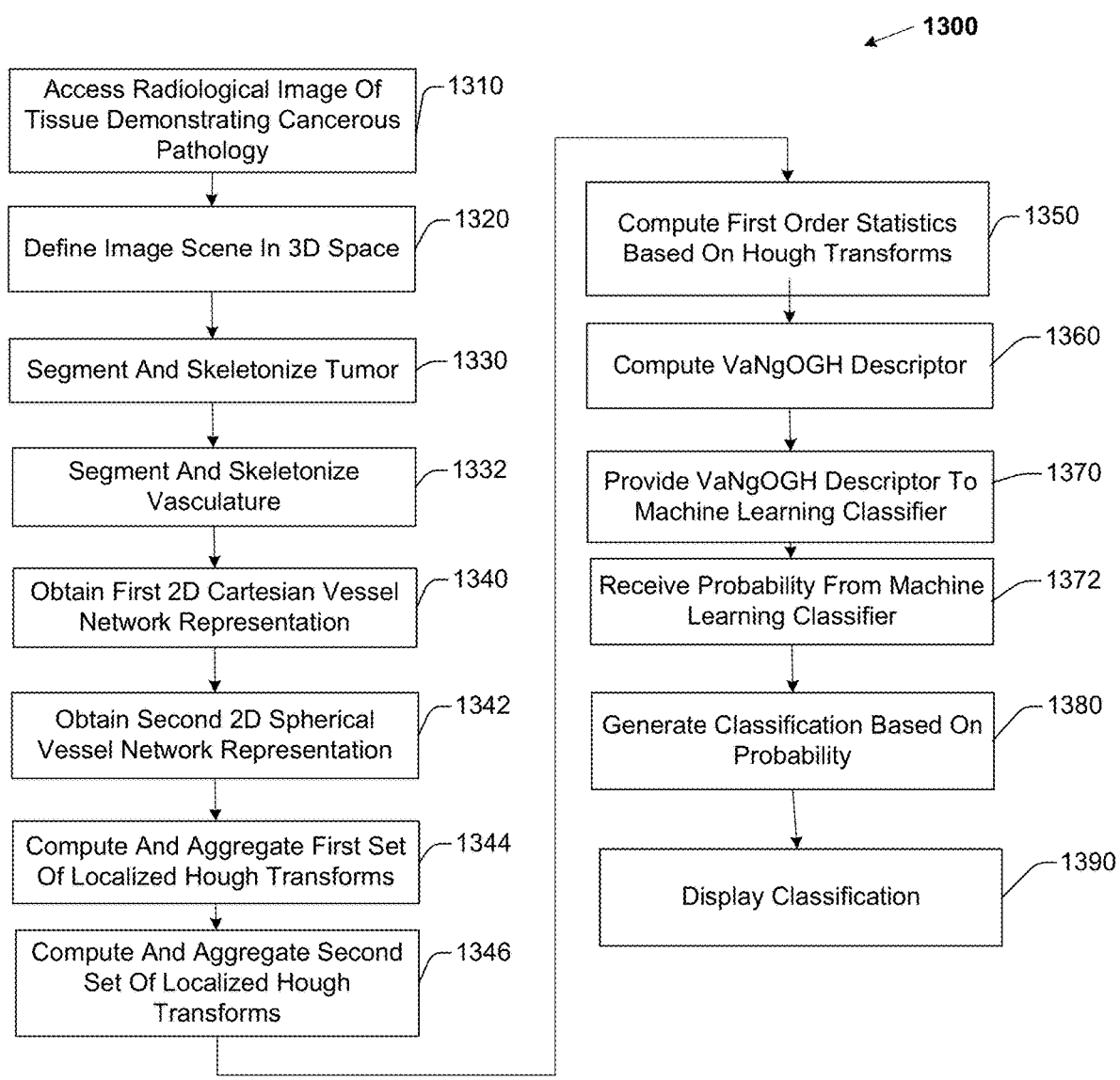
FIG. 13 illustrates an example method for distinguishing a positive class from a negative class based on the architectural disorder of a vascular architecture associated with a tumor or lesion.

FIG. 13 illustrates an example method 1300. Method 1300 includes, at 1310 accessing a digitized radiological image of a region of tissue (ROT) demonstrating cancerous pathology, where the image includes a plurality of voxels, a voxel having an intensity. Accessing the digitized radiological image includes acquiring electronic data, reading from a computer file, receiving a computer file, reading from a computer memory, or other computerized activity not practically performed in a human mind.

In one embodiment, the radiological image is a dynamic-contrast enhanced magnetic resonance imaging (DCE-MRI) image of a region of tissue demonstrating breast cancer (BCa). In another embodiment, the radiological image is a computed tomography (CT) image of a region of tissue demonstrating lung nodules.

Method 1300 also includes, at 1320, defining an image scene in a three dimensional (3D) space based on the image. The image scene includes a plurality of voxels, a voxel having an intensity. The image scene includes an intra-tumoral volume and peri-tumoral volume that is disjoint from the intra-tumoral volume. The peri-tumoral volume may include a set of peri-tumoral sub-volumes that is disjoint from the intra-tumoral volume. Defining the image scene includes acquiring electronic data, reading from a computer file, receiving a computer file, reading from a computer memory, or other computerized activity not practically performed in a human mind.

Method 1300 also includes, at 1330, segmenting and skeletonizing a tumor represented in the intra-tumoral volume. Segmenting and skeletonizing the tumor includes acquiring electronic data, reading from a computer file, receiving a computer file, reading from a computer memory, or other computerized activity not practically performed in a human mind.

Method 1300 also includes, at 1332, segmenting and skeletonizing a vasculature represented in the set of peri-tumoral sub-volumes. Segmenting and skeletonizing the vasculature may include computing a centerline of a vessel of the vasculature; and generating a medial axis skeleton S of the vasculature, where S comprises a series of points in three dimensional (3D) Cartesian space. Segmenting and skeletonizing the vasculature includes acquiring electronic data, reading from a computer file, receiving a computer file, reading from a computer memory, or other computerized activity not practically performed in a human mind.

Method 1300 also includes, at 1340 obtaining a first two-dimensional (2D) vessel network representation in the Cartesian domain from the segmented and skeletonized tumor and vasculature. Obtaining the first 2D vessel network representation includes acquiring electronic data, reading from a computer file, receiving a computer file, reading from a computer memory, or other computerized activity not practically performed in a human mind.

Method 1300 also includes, at 1342, obtaining a second 2D vessel network representation in the spherical domain from the segmented and skeletonized tumor and vasculature. Obtaining the second 2D vessel network representation includes acquiring electronic data, reading from a computer file, receiving a computer file, reading from a computer memory, or other computerized activity not practically performed in a human mind.

Method 1300 also includes, at 1344, computing and aggregating a first set of localized Hough transforms in the Cartesian space based on the first 2D vessel network representation. Computing and aggregating the first set of localized Hough transforms includes acquiring electronic data, reading from a computer file, receiving a computer file, reading from a computer memory, or other computerized activity not practically performed in a human mind.

Method 1300 also includes, at 1346, computing and aggregating a second set of localized Hough transforms on spherical projections within each member of the disjoint set of peri-tumoral sub-volumes, respectively, based on the second 2D vessel network representation. Computing and aggregating the second set of localized Hough transforms includes acquiring electronic data, reading from a computer file, receiving a computer file, reading from a computer memory, or other computerized activity not practically performed in a human mind.

Method 1300 also includes, at 1350, computing a set of first order statistics derived from the first set of localized Hough transforms and the second set of localized Hough transforms. Computing the set of first order statistics includes acquiring electronic data, reading from a computer file, receiving a computer file, reading from a computer memory, or other computerized activity not practically performed in a human mind.

Method 1300 also includes, at 1360, computing a Vascular Network Organization via Hough transform (VaNgOGH) descriptor based on the set of first order statistics. Computing the VaNgOGH descriptor includes acquiring electronic data, reading from a computer file, receiving a computer file, reading from a computer memory, or other computerized activity not practically performed in a human mind.

Method 1300 also includes, at 1370, providing the VaNgOGH descriptor to a machine learning classifier configured to distinguish a positive class from a negative class based on the VaNgOGH descriptor. In one embodiment, the machine learning classifier is an LDA classifier. In one embodiment, where the radiological image is a DCE-MRI image, the positive class is tissue that will experience pathologic complete response (pCR) following neoadjuvant chemotherapy (NAC), and the negative class is tissue that will not experience pCR following NAC. In another embodiment, where the radiological image is a CT image of lung nodules, the positive class is adenocarcinoma, and the negative class is granuloma. Providing the VaNgOGH descriptor to the machine learning classifier includes acquiring electronic data, reading from a computer file, receiving a computer file, reading from a computer memory, or other computerized activity not practically performed in a human mind.

Method 1300 also includes, at 1372, receiving, from the machine learning classifier, a probability that the region of tissue belongs to the positive class or the negative class.

Receiving the probability includes acquiring electronic data, reading from a computer file, receiving a computer file, reading from a computer memory, or other computerized activity not practically performed in a human mind.

Method 1300 also includes, at 1380, generating a classification of the region of tissue based on the probability. Generating the classification includes acquiring electronic data, reading from a computer file, receiving a computer file, reading from a computer memory, or other computerized activity not practically performed in a human mind. In one embodiment, where the radiological image is a DCE-MRI image, the classification may be pCR or non-pCR. In another embodiment, where the radiological image is a CT image of lung nodules, the classification may be granuloma or adenocarcinoma. In other embodiments, other classification schemes may be employed.

Method 1300 further includes, at 1390, displaying the classification. Displaying the classification may include displaying the classification on a computer monitor, a smartphone display, a tablet display, or other displays. Displaying the classification may also include printing the classification. In one embodiment, method 1300 further includes, at 1390, displaying at least one of the radiological image, the probability, the first 2D vessel network representation, the second 2D vessel network representation, the first set of localized Hough transforms, the second set of localized Hough transforms, the set of first order statistics, or the VaNgOGH descriptor.

Examples herein can include subject matter such as an apparatus, a pCR in BCa prediction system or apparatus, a lung nodule classification system or apparatus, a personalized medicine system, a CADx system, a processor, a system, circuitry, a method, means for performing acts, steps, or blocks of the method, at least one machine-readable medium including executable instructions that, when performed by a machine (e.g., a processor with memory, an application-specific integrated circuit (ASIC), a field programmable gate array (FPGA), or the like) cause the machine to perform acts of the method or of an apparatus or system for predicting pCR in BCa or classifying lung nodules, according to embodiments and examples described.

References to "one embodiment", "an embodiment", "one example", and "an example" indicate that the embodiment(s) or example(s) so described may include a particular feature, structure, characteristic, property, element, or limitation, but that not every embodiment or example necessarily includes that particular feature, structure, characteristic, property, element or limitation. Furthermore, repeated use of the phrase "in one embodiment" does not necessarily refer to the same embodiment, though it may.

"Computer-readable storage device", as used herein, refers to a device that stores instructions or data. "Computer-readable storage device" does not refer to propagated signals. A computer-readable storage device may take forms, including, but not limited to, non-volatile media, and volatile media. Non-volatile media may include, for example, optical disks, magnetic disks, tapes, and other media. Volatile media may include, for example, semiconductor memories, dynamic memory, and other media. Common forms of a computer-readable storage device may include, but are not limited to, a floppy disk, a flexible disk, a hard disk, a magnetic tape, other magnetic medium, an application specific integrated circuit (ASIC), a compact disk (CD), other optical medium, a random access memory (RAM), a read only memory (ROM), a memory chip or card, a memory stick, and other media from which a computer, a processor or other electronic device can read.

"Circuit", as used herein, includes but is not limited to hardware, firmware, software in execution on a machine, or combinations of each to perform a function(s) or an action(s), or to cause a function or action from another logic, method, or system. A circuit may include a software controlled microprocessor, a discrete logic (e.g., ASIC), an analog circuit, a digital circuit, a programmed logic device, a memory device containing instructions, and other physical devices. A circuit may include one or more gates, combinations of gates, or other circuit components. Where multiple logical circuits are described, it may be possible to incorporate the multiple logical circuits into one physical circuit. Similarly, where a single logical circuit is described, it may be possible to distribute that single logical circuit between multiple physical circuits.

To the extent that the term "includes" or "including" is employed in the detailed description or the claims, it is intended to be inclusive in a manner similar to the term "comprising" as that term is interpreted when employed as a transitional word in a claim.

Throughout this specification and the claims that follow, unless the context requires otherwise, the words 'comprise' and 'include' and variations such as 'comprising' and 'including' will be understood to be terms of inclusion and not exclusion. For example, when such terms are used to refer to a stated integer or group of integers, such terms do not imply the exclusion of any other integer or group of integers.

To the extent that the term "or" is employed in the detailed description or claims (e.g., A or B) it is intended to mean "A or B or both". When the applicants intend to indicate "only A or B but not both" then the term "only A or B but not both" will be employed. Thus, use of the term "or" herein is the inclusive, and not the exclusive use. See, Bryan A. Garner, A Dictionary of Modern Legal Usage 624 (2d. Ed. 1995).

While example systems, methods, and other embodiments have been illustrated by describing examples, and while the examples have been described in considerable detail, it is not the intention of the applicants to restrict or in any way limit the scope of the appended claims to such detail. It is, of course, not possible to describe every conceivable combination of components or methodologies for purposes of describing the systems, methods, and other embodiments described herein. Therefore, the invention is not limited to the specific details, the representative apparatus, and illustrative examples shown and described. Thus, this application is intended to embrace alterations, modifications, and variations that fall within the scope of the appended claims.

What is claimed is:

1. A non-transitory computer-readable storage device storing computer-executable instructions that, in response to execution, cause a processor to perform operations, the operations comprising:

accessing a radiological image of a region of interest (ROI), where the ROI includes a tumor and a peritumoral region, the image including a a plurality of voxels, a voxel having an intensity, where the image has a plane of acquisition z;

defining a tumoral volume by segmenting the tumor region represented in the image, the tumoral volume having a boundary and a centroid;

defining a peritumoral volume based on the boundary of the tumoral volume;

defining a vasculature associated with the tumoral volume, where the vasculature is located within the peritumoral volume;

generating a Cartesian two-dimensional (2D) vessel network representation in the Cartesian domain based on the vasculature;
computing a first set of localized Hough transforms based on the Cartesian 2D vessel network representation;
generating a first aggregated set of peak orientations based on the first set of localized Hough transforms;
dividing the peritumoral volume into a set of annular sub-volumes;
generating, for each annular sub-volume, respectively, a spherical 2D vessel network representation in the spherical domain based on the vasculature;
computing a second, different set of localized Hough transforms based on the spherical 2D vessel network representation of each annular sub-volume, respectively;
generating a second, different aggregated set of peak orientations based on the second set of localized Hough transforms;
generating a vascular network organization descriptor based on the first aggregated set of peak orientations and the second aggregated set of peak orientations;
providing the vascular network organization descriptor to a machine learning classifier configured to distinguish a positive class from a negative class;
receiving, from the machine learning classifier, a probability that the ROI is a member of the positive class, where the machine learning classifier computes the probability based, at least in part, on the vascular network organization descriptor;
generating a classification of the ROI as a member of the positive class or the negative class based on the probability; and
displaying the classification.

2. The non-transitory computer-readable storage device of claim 1, where defining the tumoral volume by segmenting the tumoral region includes segmenting the tumoral region using a watershed segmentation technique, region growing, an active contour technique, or a convolutional neural network (CNN).

3. The non-transitory computer-readable storage device of claim 1, where defining the vasculature comprises:
computing a centerline of a vessel of the vasculature;
generating a medial axis skeleton S of the vasculature, where S comprises a series of points in three dimensional (3D) Cartesian space.

4. The non-transitory computer-readable storage device of claim 3, where generating the Cartesian 2D vessel network representation comprises:
projecting S along the plane of image acquisition z;
generating a 2D representation of S in the XY plane.

5. The non-transitory computer-readable storage device of claim 4, where computing the first set of localized Hough transforms comprises:
for an N pixel by N pixel sliding window W with an offset of k pixels, mapping each pixel in the 2D representation of S in the XY plane to an accumulator space using a Hough transform to the 2D representation of S in the XY plane into polar co-ordinates ($\rho$, $\theta$), such that for each point in the medial axis skeleton S there exists a unique sinusoid in the accumulator space; and
identifying the top five grid locations accumulating the most sinusoid crossings for each window W.

6. The non-transitory computer-readable storage device of claim 5, where generating the first aggregated set of peak orientations based on the first set of localized Hough transforms comprises:
computing a feature set $F_{xy}$ comprising the $\theta$ values associated with the five most prominent peak orientations such that $F_{xy}=[\theta_1, \theta_2, \ldots \theta_5]$.

7. The non-transitory computer-readable storage device of claim 3, where generating the spherical 2D vessel network representation comprises:
converting S into spherical coordinates; and
generating three 2D representations of 3D vessel orientation with respect to the tumoral centroid by projecting S along each spherical dimension.

8. The non-transitory computer-readable storage device of claim 7, where:
computing the second, different set of localized Hough transforms based on the spherical 2D vessel network representation of each annular sub-volume, respectively, comprises:
computing peaks from the spherical 2D vessel network representation for each annular sub-volume; and
where generating the second, different aggregated set of peak orientations based on the second set of localized Hough transforms comprises:
generating a feature vector by concatenating peak orientations for all the annular sub-volumes.

9. The non-transitory computer readable storage device of claim 1, where generating the vascular network organization descriptor comprises concatenating first order statistics of the first aggregated set of peak orientations and the second aggregated set of peak orientations.

10. The non-transitory computer readable storage device of claim 1, where the machine learning classifier is a linear discriminant analysis (LDA) classifier configured to distinguish a positive class from a negative class.

11. The non-transitory computer readable storage device of claim 10, where the radiological image is a dynamic-contrast enhanced magnetic resonance imaging (DCE-MRI) image of a region of tissue demonstrating breast cancer (BCa).

12. The non-transitory computer readable storage device of claim 11, where the positive class is tissue that will experience pathologic complete response (pCR) following neoadjuvant chemotherapy (NAC), and where the negative class is tissue that will not experience pCR following NAC.

13. The non-transitory computer readable storage device of claim 10, where the radiological image is a computed tomography (CT) image of a region of tissue demonstrating lung nodules.

14. The non-transitory computer readable storage device of claim 13, where the positive class is adenocarcinoma, and where the negative class is granuloma.

15. The non-transitory computer readable storage device of claim 1, the operations further comprising generating a personalized cancer treatment plan based, at least in part, on the classification.

16. The non-transitory computer-readable storage device of claim 15, the operations further comprising displaying at one of the personalized cancer treatment plan, the radiological image, the tumoral volume, the vasculature, or the probability.

17. A non-transitory computer-readable storage device storing computer-executable instructions that, in response to execution, cause a processor to perform operations, the operations including:
accessing a radiological image of a region of tissue demonstrating cancerous pathology, where the image includes a plurality of voxels, a voxel having an intensity;

defining an image scene in a three dimensional (3D) space based on the image, where the image scene includes a plurality of voxels, a voxel having an intensity, where the image space includes an intra-tumoral volume and a set of peri-tumoral sub-volumes that is disjoint from the intra-tumoral volume;

segmenting and skeletonizing a tumor represented in the intra-tumoral volume;

segmenting and skeletonizing a vasculature represented in the set of peri-tumoral sub-volumes;

obtaining a first two-dimensional (2D) vessel network representation in the Cartesian domain from the segmented and skeletonized tumor and vasculature;

obtaining a second two-dimensional (2D) vessel network representation in the spherical domain from the segmented and skeletonized tumor and vasculature;

computing and aggregating a first set of localized Hough transforms in the Cartesian space based on the first 2D vessel network representation;

computing and aggregating a second set of localized Hough transforms on spherical projections within each member of the disjoint set of peri-tumoral sub-volumes, respectively, based on the second 2D vessel network representation;

computing a set of first order statistics derived from the first set of localized Hough transforms and the second set of localized Hough transforms;

computing a Vascular Network Organization via Hough transform (VaNgOGH) descriptor based on the set of first order statistics;

providing the VaNgOGH descriptor to a machine learning classifier configured to distinguish a positive class from a negative class based on the VaNgOGH descriptor; and receiving a probability that the region of tissue belongs to the positive class or the negative class;

generating a classification of the region of tissue based on the probability; and displaying the classification.

18. The non-transitory computer-readable storage device of claim 17, where the radiological image is a dynamic-contrast enhanced magnetic resonance imaging (DCE-MRI) image of a region of tissue demonstrating breast cancer (BCa), and where the positive class is tissue that will experience pathologic complete response (pCR) following neoadjuvant chemotherapy (NAC), and where the negative class is tissue that will not experience pCR following NAC.

19. The non-transitory computer-readable storage device of claim 17, where the radiological image is a computed tomography (CT) image of a region of tissue demonstrating lung nodules; and where the positive class is adenocarcinoma, and where the negative class is granuloma.

20. An apparatus comprising:
a processor;
a memory configured to store a digitized radiological image of a region of interest (ROI) demonstrating cancerous pathology, the digitized radiological image having a plurality of voxels, a voxel having an intensity;
an input/output (I/O) interface;
a set of circuits; and
an interface that connects the processor, the memory, the I/O interface, and the set of circuits, the set of circuits comprising:

an image acquisition circuit configured to:
access a digitized radiological image of an ROI, where the ROI includes a tumor and a peritumoral region, the image including a a plurality of voxels, a voxel having an intensity, where the image has a plane of acquisition z a segmentation and skeletonization circuit configured to:
define a tumoral volume by segmenting the tumor region represented in the image, the tumoral volume having a boundary and a centroid;
define a peritumoral volume based on the boundary of the tumoral volume; and
define a vasculature associated with the tumoral volume, where the vasculature is located within the peritumoral volume;

a Cartesian feature circuit configured to:
generate a Cartesian two-dimensional (2D) vessel network representation in the Cartesian domain based on the vasculature;
compute a first set of localized Hough transforms based on the Cartesian 2D vessel network representation; and
generate a first aggregated set of peak orientations based on the first set of localized Hough transforms;

a spherical domain feature circuit configured to:
divide the peritumoral volume into a set of annular sub-volumes;
generate, for each annular sub-volume, respectively, a spherical 2D vessel network representation in the spherical domain based on the vasculature;
compute a second, different set of localized Hough transforms based on the spherical 2D vessel network representation of each annular sub-volume, respectively; and
generate a second, different aggregated set of peak orientations based on the second set of localized Hough transforms;

a vascular network organization descriptor circuit configured to:
generate a vascular network organization descriptor based on the first aggregated set of peak orientations and the second aggregated set of peak orientations;

a classification circuit configured to:
compute a probability that the ROI is a member of a positive class or negative class, where the classification circuit is configured to compute the probability based, at least in part, on the vascular network organization descriptor, using a linear discriminant analysis (LDA) machine learning approach; and
generate a classification of the ROI as a member of the positive class or the negative class based on the probability; and a display circuit configured to display the classification.

21. The apparatus of claim 20, where the digitized radiological image of an ROI is a dynamic-contrast enhanced magnetic resonance imaging (DCE-MRI) image of a region of tissue demonstrating breast cancer (BCa), and where the positive class is tissue that will experience pathologic complete response (pCR) following neoadjuvant chemotherapy (NAC), and where the negative class is tissue that will not experience pCR following NAC.

22. The apparatus of claim 20, where the digitized radiological image of an ROI is a computed tomography (CT) image of a region of tissue demonstrating lung nodules; and where the positive class is adenocarcinoma, and where the negative class is granuloma.

* * * * *

UNITED STATES PATENT AND TRADEMARK OFFICE
CERTIFICATE OF CORRECTION

PATENT NO. : 10,861,152 B2
APPLICATION NO. : 16/354504
DATED : December 8, 2020
INVENTOR(S) : Anant Madabhushi et al.

It is certified that error appears in the above-identified patent and that said Letters Patent is hereby corrected as shown below:

In the Specification

Column 1, Lines 15 through 23; please replace "This invention was made with government support under the grant(s) F31CA221383-01A1, 1U24CA199374-01, R01CA202752-01A1, R01CA208236-01A1, R21CA179327-01, R21CA195152-01, RO1 DK098503-02, 1C06-RR12463-01, PC120857, LC130463, and T32EB007509 awarded by the National Institutes of Health Also grant W81XWH-16-1-0329 awarded by the Department of Defense. The government has certain rights in the invention." with --This invention was made with government support under the grant(s) CA179327, CA195152, CA199374, CA202752, CA208236, CA221383, DK098503, EB007509, and RR012463 awarded by the National Institutes of Health; and grant(s) W81XWH-13-1-0418, W81XWH-14-1-0323, and W81XWH-16-1-0329 awarded by the Department of Defense. The government has certain rights in the invention.--

Signed and Sealed this
Fourteenth Day of September, 2021

Drew Hirshfeld
*Performing the Functions and Duties of the
Under Secretary of Commerce for Intellectual Property and
Director of the United States Patent and Trademark Office*